United States Patent [19]

Nishizawa et al.

[11] Patent Number: 4,645,572

[45] Date of Patent: Feb. 24, 1987

[54] METHOD OF DETERMINING CONCENTRATION OF A COMPONENT IN GASES AND ELECTROCHEMICAL DEVICE SUITABLE FOR PRACTICING THE METHOD

[75] Inventors: Hitoshi Nishizawa; Yoshihiko Mizutani, both of Nagoya, Japan

[73] Assignee: NGK Insulators, Ltd., Japan

[21] Appl. No.: 831,707

[22] Filed: Feb. 20, 1986

[30] Foreign Application Priority Data

Feb. 23, 1985 [JP] Japan ................................ 60-35124
Apr. 19, 1985 [JP] Japan ................................ 60-85249

[51] Int. Cl.⁴ .......................................... G01N 27/58
[52] U.S. Cl. .................................... 204/1 T; 204/406; 204/410; 204/412; 204/425
[58] Field of Search ............... 204/406, 410, 412, 425, 204/15

[56] References Cited

U.S. PATENT DOCUMENTS

| 4,264,425 | 4/1981 | Kimura et al. ................. 204/425 |
| 4,272,329 | 6/1981 | Hetrick et al. ................. 204/1 T |
| 4,498,968 | 2/1985 | Yamada et al. ................ 204/412 |
| 4,578,171 | 3/1986 | Yamada et al. ................ 204/406 |
| 4,578,172 | 3/1986 | Yamada et al. ................ 204/412 |
| 4,591,421 | 5/1986 | Yamada et al. ................ 204/406 |
| 4,594,139 | 6/1986 | Asayama et al. .............. 204/410 |

FOREIGN PATENT DOCUMENTS

| 0066853 | 12/1982 | European Pat. Off. ............ 204/425 |
| 0127964 | 12/1984 | European Pat. Off. ............ 204/425 |
| 0138170 | 4/1985 | European Pat. Off. ............ 204/425 |
| 0147988 | 7/1985 | European Pat. Off. ............ 204/425 |
| 3405576 | 1/1985 | Fed. Rep. of Germany ...... 204/425 |

Primary Examiner—G. L. Kaplan
Attorney, Agent, or Firm—Parkhurst & Oliff

[57] ABSTRACT

A method of detecting the concentration of a component in gases, by an electrochemical element comprising a pumping cell having a first and a second electrode on a solid electrolyte layer, and a sensing cell comprising a third and a fourth electrode disposed on another solid electrolyte layer, the first and third electrodes being located adjacent to each other, and exposed to the gas to be measured which has been diffused with a predetermined diffusion resistance. A primary pumping current is applied to the pumping cell to control the partial pressure of the component in the atmosphere adjacent to the first and third electrodes. The primary pumping current is controlled so that an electromotive force induced on the sensing cell concides with a predetermined value. The method comprises a step of applying an auxiliary pumping current between the third electrode of the sensing cell, and one of the other three electrodes, for effecting an auxiliary pumping operation so as to cause a change in the partial pressure of the component in the atmosphere adjacent to the third electrode, in the same direction as a change in the partial pressure in the atmosphere adjacent to the first electrode, which is caused by the primary pumping current. Also disclosed is an electrochemical device for practicing the method.

27 Claims, 29 Drawing Figures

METHOD OF DETERMINING CONCENTRATION OF A COMPONENT IN GASES AND ELECTROCHEMICAL DEVICE SUITABLE FOR PRACTICING THE METHOD

BACKGROUND OF THE INVENTION

1. Field of the Invention

The present invention relates in general to a method of determining or detecting the concentration of a component in a gas to be measured, by using a solid electrolyte, and to a electrochemical device suitable for practicing the method. More particularly, the invention is concerned with such method and device for determining the concentration of a given component in the gas to be measured, by utilizing two electrochemical cells as a pumping and sensing cell, each cell comprising a solid electrolyte body and a pair of porous electrodes.

2. Related Art Statement

There are known various types of electrochemical devices or elements using a solid electrolyte material, for example, as A/F ratio sensors for determining the concentration of oxygen or unburned components in exhaust gases produced by an internal combustion engine or a motor vehicle. Such an A/F ratio sensor, which detects an A/F (air/fuel) ratio of an air-fuel mixture supplied to the engine, comprises an electrochemical cell which employs, for example, zirconia ceramics as an oxygen-ion conductive solid electrolyte, and a pair of porous electrodes. The electrochemical cell is adapted to perform a well-known electrochemical pumping action by electrode reaction due to an electric current applied between the pair of electrodes. Meanwhile, one of the electrodes is exposed to the gas (exhaust gases) in an external space, via suitable diffusion-resistance means as in the form of a thin flat space or clearance or a porous ceramic layer, which has a predetermined diffusion resistance to the molecules of the component to be measured. The pumping current flowing through the electrodes represents the concentration of the component such as oxygen or unburned components in the external gas, whereby the concentration is determined. Also known in the art are detectors (electrochemical devices) which are adapted to sense, like the A/F sensors indicated above, various other substances such as water, hydrogen and carbon dioxides.

In such a method of determining the concentration of a given component in a gas, through measurement of an amount of diffusion of the component which varies with the concentration of the component, by using an electrochemical element of a single cell type having a single electrochemical cell (pumping cell) with diffusion-resistance means, there is a problem that an electromotive force which is induced according to the principle of a concentration cell and which is measured as an output indicative of a partial pressure of the component to be measured or the component which reacts with the component to be measured, will have an error due to resistance polarization by a pumping current flowing through the electrochemical cell.

To solve the problem with the method using an electrochemical element of a single cell type, a method is proposed which uses an electrochemical element of a double cell type which comprises two electrochemical cells each constructed as previously described. In this method, one of the cells is adapted to serve as an electrochemical pumping cell, while the other cell is adapted to serve as an electrochemical sensing cell, so that the varying concentration of the desired component is determined by measuring an accordingly varying amount of diffusion of the component.

In the above-indicated double cell type of electrochemical element, the electrochemical pumping cell attains an electrochemical pumping action by electrode reaction due to an electric current flowing through its pair of electrodes, so as to control an atmosphere surrounding the electrode which is exposed to the gas in an external space through the diffusion-resistance means. On the other hand, the electrochemical sensing cell is adapted to detect an electromotive force which is induced, according to the principle of a concentration cell, due to a difference in partial pressure of the component to be measured or the component which reacts with the component to be measured between the atmospheres which contact the pair of electrodes of the sensing cell (one of these electrodes being exposed to the atmosphere controlled by the pumping cell indicated above). The pumping current applied to the electrochemical pumping cell is controlled so that the detected electromotive force is equal to a predetermined value. The concentration of the component in the gas to be measured is determined by the amount of controlled pumping current. Alternatively, a predetermined amount of pumping current is applied to the pumping cell to control the atmosphere surrounding one of the pumping electrodes, so that an electromotive force corresponding to the thus controlled atmosphere is measured by the electrochemical sensing cell, as an output signal of if the concentration of the component to be measured is more or less than the value which is represented by said pumping current.

3. Problem Solved by the Invention

However, the method of determining the concentration of a component in a gas by using an electrochemical element of the double cell type, suffers inconveniences as described below. That is, the atmosphere to which one of the electrodes of the pumping cell (i.e., inner pumping electrode) and one of the electrodes of the sensing cell (i.e., measuring electrode) are exposed tends to have a difference in concentration of a gas component because the two electrodes are spaced from each other. Further, there exists a difference in the concentration, due to a resistance of diffusion of porous structures such as a porous protective layer covering the electrodes, or the porous electrodes themselves. Consequently, there arises a difference in a partial pressure of the component to be measured or the component which reacts with the component to be measured between the atmosphere adjacent to the inner pumping electrode of the pumping cell and the atmosphere adjacent to the measuring electrode of the sensing cell. This difference results in errors in the measurements, and to deterioration of the pumping cell where the electrochemical element is applied to detect lean-burned exhaust gases (particularly, exhaust gases having an oxygen concentration as high as ambient air). In particular, when the electrochemical element is used to determine the concentration of oxygen in an atmosphere which, like dry air, consists of inert gases and oxygen only, the oxygen partial pressure adjacent to the inner pumping electrode is far lower than that adjacent to the measuring electrode. If, in this case, the atmosphere adjacent to the measuring electrode is controlled so as to have a low oxygen partial pressure, the atmosphere adjacent to the inner pumping electrode is extremely deficient in oxygen, whereby the zirconia solid electrolyte near the inner pumping electrode is subject to severe reduction and accordingly deteriorated.

SUMMARY OF THE INVENTION

It is therefore an object of the present invention to provide improved method and device for determining the concentration of a component in a gas by means of a solid electrolyte body and electrodes, which are substantially free from the above-indicated inconveniences experienced in the prior art.

According to the present invention, there is provided a method of determining the concentration of a component in a gas, by an electrochemical element which includes: an electrochemical pumping cell comprising a first solid electrolyte body, and a first and a second porous electrode disposed on the first electrolyte body; an electrochemical sensing cell comprising a second solid electrolye body, and a third and a fourth porous electrode disposed on the second solid electrolyte body, the third electrode being positioned near the first electrode of the pumping cell; and diffusion-resistance means having a predetermined diffusion resistance to the molecules of the component in the gas in an external space, the diffusion-resistance means permitting the gas to diffuse therethrough with the diffusion resistance, for contact with the first and third electrodes of the pumping and sensing cells, the method comprising a step of controlling a pumping current to be applied to the pumping cell to effect an electrochemical pumping operation, so that an electromotive force which is induced on the sensing cell, according to the principle of a concentration cell, based on a partial pressure of the component in an atmosphere adjacent to the third electrode, coincides with a predetermined value, a step of detecting the controlled pumping current, and a step of determining the concentration of the component in the gas, based on the detected pumping current, the method further comprising the step of: applying an auxiliary pumping current between the third electrode of the sensing cell, and one of the other electrodes, for effecting an auxiliary pumping operation so as to change the partial pressure of the component in the atmosphere adjacent to the third electrode, in a direction in which the partial pressure of the component in an atmosphere adjacent to the first electrode is changed by the electrochemical pumping operation of the pumping cell.

In other words, the polarity of the first electrode and the third electrode is the same for the primary and the auxiliary pumping operation, i.e. the third electrode works as the cathode of the auxiliary pumping operation when the first electrode works as the cathode of the primary pumping operation, and works as the anode of the auxiliary pumping operation when the first electrode works as the anode of the primary pumping operation.

According to another aspect of the invention, there is provided an electrochemical device suitable for practicing the method of the invention, including: an electrochemical pumping cell comprising a first solid electrolyte body, and a first and a second porous electrode disposed on the first solid electrolyte body; an electrochemical sensing cell comprising a second solid electrolyte body, and a third and a fourth porous electrode disposed on the second solid electrolyte body, the third electrode being positioned near the first electrode of the pumping cell and being electrically connected to said first electrode of the pumping cell; and diffusion-resistance means having a predetermined diffusion resistance to the molecules of the component in the gas in an external space, the diffusion-resistance means permitting the gas to diffuse therethrough with the diffusion resistance, for contact with the first and third electrodes of the pumping and sensing cells; means for applying a pumping current between the first and second electrodes of the pumping cell to effect an electrochemical pumping operation, for controlling a partial pressure of the component in an atmosphere adjacent to the first electrode; and means for detecting a potential difference which is induced between the third and fourth electrodes, due to a difference between the controlled partial pressure of the component in the atmosphere adjacent to the third electrode, and a partial pressure of the component in the atmosphere adjacent to the fourth electrode, the pumping and sensing cells forming an electrochemical element, the electrochemical device comprising: electrically resistant means which electrically separates the first and second solid electrolyte bodies from each other, the electrically resistant means having an opening which is located adjacent to at least one of the first and third electrodes and which permits the first and second solid electrolyte bodies to be electrically connected partially to each other, whereby the potential difference between the third and fourth electrodes is detected.

In the electrochemical device constructed as described above, the first and second solid electrolyte bodies are electrically separated or insulated from each other by the electrically resistant means. Further, the opening formed in the electrically resistant means permits electrical connection of the first and second solid electrolyte bodies at a point adjacent to the first and/or third electrode(s). In this arrangement, a potential of the first solid electrolyte in the vicinity of the opening of the electrically resistant means is primarily detected, according to the principle of a Luggin capillary in an electrolyte solution. Therefore, it is possible to considerably reduce an influence of resistance polarization due to a pumping current between the first and second electrodes, on a potential difference between the third and fourth electrodes.

The present invention is effective particularly when the gas to be measured is a gas, such as dry air, which consists of a component to be measured (oxygen) and inert gases (nitrogen, etc.), namely, where a difference in partial pressure of the measurement component according to the principle of a concentration cell is likely to exist within the atmosphere to which the first electrode of the pumping cell and the third electrode of the sensing cell are both exposed, for example, within an internal cavity formed in the electrochemical element. The solid electrolyte of the element is easily deteriorated in such conditions, due to a relatively large partial pressure difference. A solution to this problem is provided by the present invention wherein a slight degree of electrochemical pumping operation is achieved between the third electrode of the sensing cell, and one of the other electrodes, for the purpose of reducing the above-indicated partial pressure difference, and consequently protecting the solid electrolyte body of the pumping cell. That is, an auxiliary current is applied to the third electrode of the sensing cell, an amount of the auxiliary current being controlled corresponding to an amount of the primary pumping current applied to the pumping cell. Thus, the present invention makes it possible to minimize the difference in partial pressure of the component to be measured or the component which reacts with the component to be measured between the atmospheres adjacent to the first and third electrodes of the pumping and sensing cells, whereby the accuracy of measurement is improved for all kinds of atmospheres to be handled by the electrochemical device.

Since the above-indicated partial pressure difference of the component between the atmospheres adjacent to the first electrode (inner pumping electrode) and the third electrode (measuring electrode) corresponds to a relatively small difference in concentration of the component, the above-described effect may be offered even when the amount of auxiliary pumping current to be applied to the third electrode is relatively small as compared with the primary pumping current to be applied to the pumping cell. Accordingly, the output voltage (electromotive force) of the sensing cell is least influenced by the resistance polarization due to the auxiliary pumping current. In this sense, the present invention may be practiced without sacrificing the advantages which are offered on an electrochemical element of a double-cell type (using a pumping and a sensing cell).

BRIEF DESCRIPTION OF THE DRAWINGS

The foregoing and optional objects, features and advantages of the present invention will be better understood from reading the following detailed description of preferred embodiments of the invention, when considered in connection with the accompanying drawings, wherein.

DETAILED DESCRIPTION OF THE PREFERRED EMBODIMENTS

Figure 1:
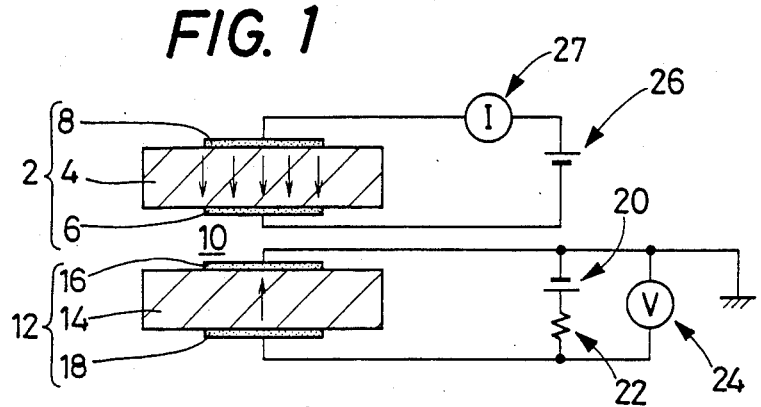
FIGS. 1, 2 and 3 are schematic representations illustrating three different embodiments of a method of this invention, respectively.

Referring first to FIG. 1, there is shown an embodiment of the invention showing its principle, in which an auxiliary pumping current is applied between a third and a fourth electrode of an electrochemical sensing cell, so as to effect an auxiliary pumping action. Described more specifically, an electrochemical pumping cell 2 consits of a first planar solid electrolyte body 4, and a first and a second porous electrode 6, 8 which are disposed on opposite surfaces of the first solid electrolyte body 4. In the meantime, an electrochemical sensing cell 12 consists of a second planar solid electrolyte body 14, and a third and a fourth porous electrode 16, 18 disposed on opposite surfaces of the second solid electrolyte body 14. The electrochemical puming cell 2 and the electrochemical sensing cell 12 cooperate to form an electrochemical element which has an internal cavity 10 to which are exposed the first electrode 6 of the pumping cell 2 and the third electrode 16 of the sensing cell 12. The internal cavity 10 communicates, via suitable diffusion-resistance means, with an external space in which a gas to be measured exists. The diffusion-resistance means has a predetermined diffusion resistance to the molecules of a given component in the gas, and the gas is introduced through the diffusion-resistance means into the internal cavity 10, with the predetermined diffusion resistance.

The third and fourth electrodes 16, 18 of the sensing cell 12 are connected via a resistor 22 to a DC power source 20 for auxiliary pumping, so that a predetermined amount of DC current is applied as an auxiliary pumping current between these two electrodes 16, 18. A voltmeter 24 is also connected to the fourth electrode 18 which is exposed to a reference gas, and to the third electrode 16 which is exposed to the atmosphere in the internal cavity 10. The voltmeter 24 detects an electromotive force which is induced, according to the principle of a concentration cell, due to a difference in the partial pressure of the component to be measured or the component which reacts with the component to be measured between the reference gas and the atmosphere in the cavity 10. Meanwhile, a power source 26 is connected to the first and second electrodes 6, 8 of the pumping cell 2 which operates to control the atmosphere in the cavity 10. The power source 26 causes a predetermined amount of pumping current to be applied as a primary pumping current between the electrodes 6, 8. This pumping current is measured by an ammeter 27 connected between the second electrode 8 and the power source 26.

In the above-described embodiment, the concentration of the gas component in the atmosphere adjacent to the first electrode 6 exposed to the internal cavity 10 is varied by a primary pumping action of the pumping cell 2, that is, by an electrochemical pumping operation between the first and second electrodes 6, 8 upon application of a DC current from the power source 26 to the electrodes 6, 8. In the meantime, an auxiliary pumping operation due to an auxiliary pumping current flowing through the third and fourth electrodes 16, 18 of the sensing cell 2, will cause the atmosphere surrounding the third electrode 16 to be varied in the same direction as the atmosphere surrounding the first electrode 6. Therefore, a difference in partial pressure of the component to be measured which would exist between the atmospheres surrounding the first and third electrodes 6, 16 in the internal cavity 10 will be effectively minimized or removed by the auxiliary pumping action performed between the third and fourth electrodes 16, 18.

Stated differently, when the partial pressure of the component to be measured in the atmosphere surrounding the first electrode 6 of the pumping cell 2 is reduced, the partial pressure of the component to be measured in the atmosphere surrounding the third electrode 16 of the sensing cell 12 is also reduced due to the auxiliary pumping action. In the same way, the partial pressure adjacent to the third electrode 16 is increased when the partial pressure adjacent to the electrode 6 is increased. Hence, the difference in the partial pressure of the component to be measured between the atmospheres adjacent to the first and third electrodes 6, 16 can be held as small as possible.

Figure 2:
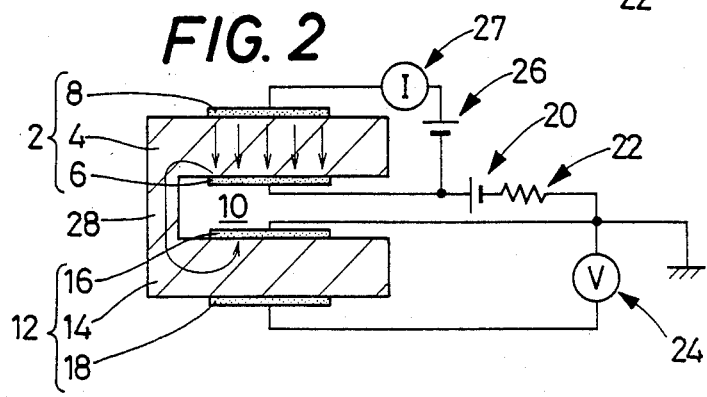

Referring next to FIG. 2, there is illustrated a second embodiment of the method for practicing the principle of the invention, in which the first solid electrolyte body 4 of the pumping cell 2 and the second solid electrolyte body 14 of the sensing cell 12 are electrically connected to each other at a part indicated at 28, either directly or by another solid electrolyte body. In this example, an auxiliary pumping current is applied, through the connecting part 28, between the first and third electrodes 6, 16 of the pumping and sensing cells 2, 12. Described in more detail, the power source 20 for auxiliary pumping action is provided in a circuit which includes the first electrode 6, first solid electrolyte body 4, connecting part 28, second solid electrolyte body 14 and third electrode 16. With an auxiliary pumping current applied by the power source 20 between the first and third electrodes 6, 16, the partial pressure of the measurement component in the atmosphere surrounding the third electrode 16 is changed so as to reduce the difference in the partial pressure between the atmospheres adjacent to the two electrodes 6, 16.

Figure 3:
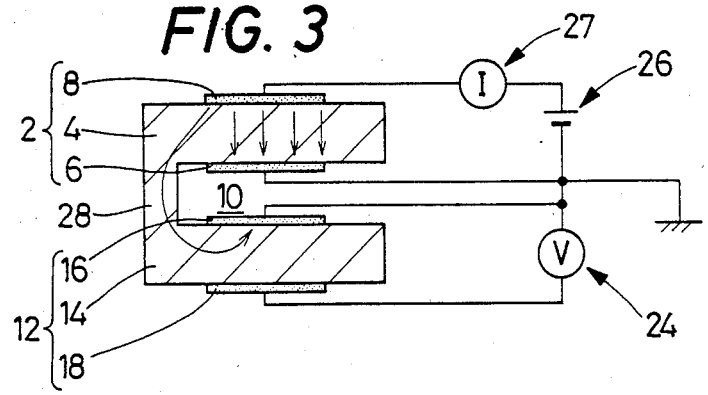

In a third embodiment of the invention shown in FIG. 3, the first and second solid electrolyte bodies 4, 14 of the pumping and sensing cells 2, 12 are electrically connected at the connecting part 28, as in the embodiment of FIG. 2, while the first and third electrodes 6, 16 are electrically connected to each other so that a portion of the pumping current flowing through the pumping cell 2 is permitted to pass through the third electrode 16 of the sensing cell 12 via the connecting part 28.

Stated in greater detail, the pumping power source 26 is provided in a circuit which includes the second electrode 8, first solid electrolyte body 4, connecting part 28, second electrolyte body 14 and third electrode 16.

In this arrangement, therefore, a part of the pumping current flowing through the second electrode 8 is permitted to leak through the third electrode 16. Accordingly, an auxiliary pumping action may take place between the second and third electrodes 8, 16, and consequently the partial pressure of the component to be measured in the atmosphere surrounding the third electrode 16 is changed so as to reduce the partial pressure difference between the first and third electrodes 6, 16, in a manner similar to that in the embodiment of FIG. 2.

In connection with the first and third embodiments of FIGS. 1 and 3 adapted to implement the principle of the invention, it is possible to use, for certain applications, a common electrode which serves as the first and third electrodes 6 and 16. Namely, it is possible to effect a primary electrochemical pumping operation between the common electrode (first and third electrodes) and the second electrode 8. In this case, a part of the common electrode at which the density of the pumping current is comparatively low is used as a measuring electrode which cooperates with the fourth electrode to constitute a sensing cell, in which an electromotive force is measured between that measuring electrode and the fourth electrode, so that a pumping action will not influence the output of an electromotive force of the sensing cell. In this modified arrangement of the first and third embodiments, too, an auxiliary pumping operation is performed between the inner pumping part and the measuring part of the common electrode, in order to reduce the partial pressure difference between the pumping and measuring part of the common electrode.

In determining the concentration of the component in a given gas according to the above-described three different embodiments of the invention, a primary pumping current to be applied to the pumping cell 2 is controlled in response to the level of an electromotive force induced on the sensing cell 12 (detected by the voltmeter 24). That is, the primary pumping current is varied so that the detected electromotive force coincides with a predetermined level. If, at this time, the electric current flowing through the third electrode 16 of the sensing cell 12, i.e., an auxiliary pumping current is also varied, it is preferred that the magnitude of resistance polarization due to the auxiliary pumping current be held not greater than the level of an electromotive force which is induced on the sensing cell 12 according to the principle of a concentration cell. Preferably, the resistance polarization due to the auxiliary pumping action is held less than 50% of electromotive force induced on the sensing cell 12. In the case where the auxiliary pumping current is held constant, however, the magnitude of the resistance polarization may exceed the level of an electromotive force induced according to the principle of a concentration cell. In this instance, the threshold level or value of the electromotive force of the sensing cell 12 is set to be greater than the value of the resistance polarization due to the auxiliary pumping action.

Figure 9:
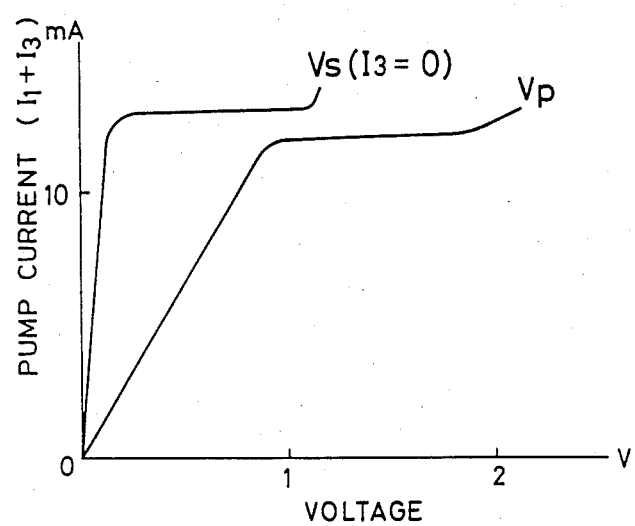
FIGS. 9 and 10 are graphs showing relationships between a pumping current of a pumping cell and terminal voltages of a pumping cell and a sensing cell, respectively.

As described above, an auxiliary pumping current is applied to reduce a partial pressure difference between the atmospheres surrounding the first and third electrodes 6, 16. In this connection, there will be described relations among a pumping voltage $V_p$ applied to the pumping cell 2, a primary pumping current $I_1$ (flowing through the first electrode 6), and an electromotive force $V_s$ of the sensing cell 12. If the auxiliary pumping current $I_3$ is not applied ($I_3=0$), the level of a limiting current on a $V_p$ vs. $(I_1+I_3)$ curve (a point at which the atmosphere surrounding the first electrode 6 is changed) is lower than the level of a limiting current on a Vs vs. ($I_1+I_3$) curve (a point at which the atmosphere surrounding the electrode 16 is changed), as indicated in FIG. 9. This indicates that the atmosphere adjacent to the first electrode 6 is more likely to be changed than the atmosphere adjacent to the third electrode 16.

Figure 10:
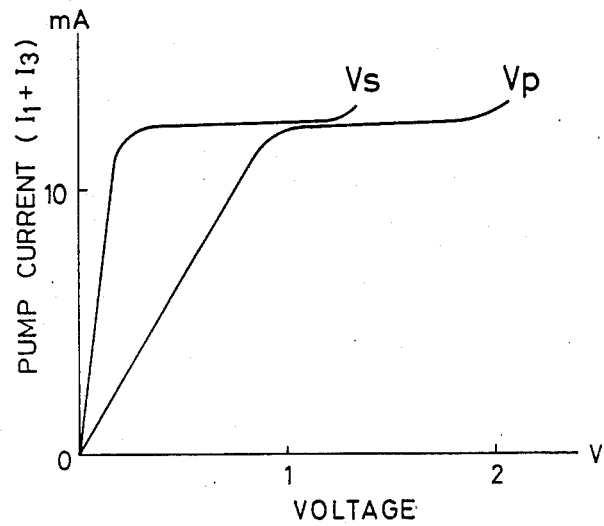

As the value $I_3$ is gradually increased (with a result of reducing the value $I_1$), a difference in the limiting current on the two curves is reduced to zero, as indicated in FIG. 10. Finally, the limiting current on the Vs vs. ($I_1+I_3$) curve finally falls below the limiting current on the Vp vs. ($I_1+I_3$) curve. An optimum ratio of $I_1$ to $I_3$ is selected so that the two limiting current values are equal to each other. This ratio allows the measurement with a minimum error, and maximum durability of the electrochemical element.

The value of $I_3$ which satisfies the above optimum ratio is difficult to be settled at a fixed point, that is, varied depending upon various factors which include: configuration of diffusion-resistance means and its diffusion resistance; relative positions, configuration, and surface areas of the first and third electrodes 6, 16; configuration of the internal cavity 10 to which the electrodes 6, 16 are exposed; thickness and porosity of the porous electrodes and a porous layer covering the electrodes. Since an increase in the auxiliary pumping current $I_3$ will cause an increaes in the degree of resistance polarization of a sensing cell and will leads to diminishing the advantages of an electrochemical element of a double cell type, it is generally desired to determine the auxiliary pumping current $I_3$ so that an average density $J_3$ (mA/mm$^2$) of the auxiliary pumping current $I_3$ is not higher than than an average density $J_1$ (mA/mm$^2$) of the primary pumping current $I_1$ ($J_3 \geq J_1$). It has been confirmed that the values $J_3 \geq 2 \times 10^{-3} \times J_1$ are effective for the reduction of a difference between the limiting currents which correspond to Vs and Vp. That is, the auxiliary pumping current $I_3$ should be selected with the value $J_3$ held preferably within the following range:

$$2 \times 10^{-3} \times J_1 \leq J_3 \leq J_1,$$

and more preferably within the following range:

$$5 \times 10^{-3} \times J_1 \leq J_3 \leq 0.5 \times J_1.$$

By applying the thus selected amount of auxiliary current to the third electrode 16 of the sensing cell 12, it is possible to reduce the partial pressure difference between the atmospheres adjacent to this third electrode 16 and the first electrode 6 of the pumping cell 2. Thus, the application of the auxiliary pumping current provides for (A) an improvement in the measuring accuracy of the electrochemical element, and (B) an improvement in the durability of the electrochemical element, namely, complete elimination or minimization of decomposition of the first solid electrolyte body 4 at its part adjacent to the first electrode 6, due to extreme reduction in concentration of conductive ions adjacent to the first electrode 6, while the ions are pumped out from the first electrode 6 toward the second electrode 8. If the improvement (A) is particularly desired, it is effective to control the auxiliary pumping current in proportion to, or as a function of the pumping current applied to the pumping cell 2. In the case where the improvement (B) is particularly desired, it is required to apply the auxiliary pumping current while the conductive ions are pumped out from the side of the first electrode 6, especially where the gas to be measured consists of a mixture of the component including conductive ion and inert components. In this case, it is not necessary to apply the auxiliary pumping current, while the ions are pumped in toward the first electrode 6, or while the level of the pumping current is low.

In one preferred form of the invention wherein an auxiliary pumping current is applied as discussed hitherto, the concentration of the component to be measured in the gas is determined by detecting an amount of electric current which corresponds to the entire amount of diffusion of the component to be measured, more specifically, by detecting a sum of the current flowing through the first electrode 6 of the pumping cell 2, and the current flowing through the third electrode 16 of the sensing cell 16.

Referring next to FIGS. 4 through 8, there are shown different basic arrangements of an electrochemical element for practicing the principle of the invention according to the third embodiment of FIG. 3.

Figure 4:
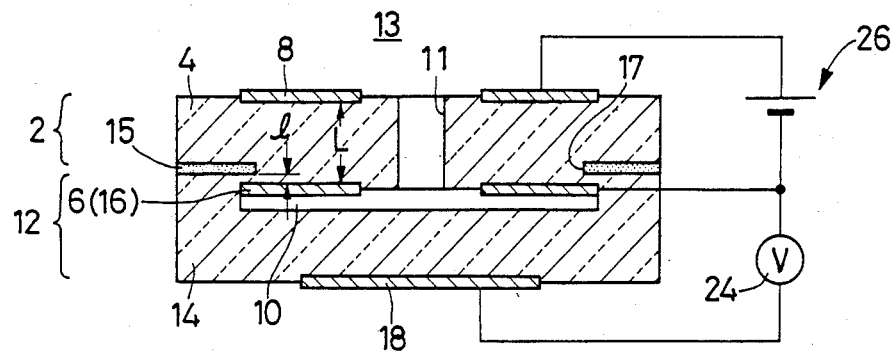
FIGS. 4 through 8 are schematic views in cross section of different basic arrangements of an electrochemical device constructed according to the invention, respectively.

In the first arrangement shown in FIG. 4, reference numerals 4 and 14 indicate respectively the first and second planar solid electrolyte bodies which cooperate to define the internal cavity 10 in the form of a thin flat gas space that serves as diffusion-resistance means. The gas space 10 communicates with an external space 13 through an aperture 11 formed through a central part of the solid electrolyte body 4. In this arrangement, the gas existing in the external space 13 is introduced into the gas space 10 through the aperture 11 which is open in the central part of the space 10. The gas component which has been introduced into the central part of the space 10, diffuses toward the periphery of the space 10 with a predetermined diffusion resistance that is determined by the thickness of the space 10.

On opposite surfaces of the solid electrolyte body 4, the first electrode 6 (third electrode 16) and the second electrode 8 in the form of annular electrodes are disposed concentrically with each other such that the electrodes surround the opposite open ends of the aperture 11 and are exposed to the gas space 10 and the external space 13, respectively. The fourth electrode 18 is disposed on an outer surface of the solid electrolyte body 14 remote from the gas space 10. Electrically resistant or resistive means in the form of an insulating layer 15 with a high electric resistance is formed between the solid electrolyte bodies 4, 14. The insulating layer 15 has a round opening indicated at 17, which has a diameter slightly smaller than the outside diameter of the first (third) electrode 6(16). The insulating layer 15 is spaced from the first (third) electrode 6(16) toward the second electrode 8 by a slight distance in the direction of thickness. The insulating layer 15 is positioned so that its opening 17 is aligned or concentric with the electrode 6(16). Thus, the insulating layer 15 is located so as to electrically separate the first and second solid electrolyte bodies 4, 14 at their connecting part defining the outer periphery of the gas space 10.

The pumping power source 26 is connected between the first and second electrodes 6(16) and 8 so that a suitable amount of DC pumping current flows from one of these electrodes to the other so as to effect a primary electrochemical pumping operation therebetween, which permits a control of the atmosphere adjacent to the first (third) electrode 6(16). In the meantime, the voltmeter 24 is connected to the third (first) electrode 16(6) exposed to the atmosphere in the gas space 10, and the fourth electrode 18 exposed to the gas in the external space as a reference gas. Thus, the voltmeter 24 is adapted to detect an electromotive force which is induced between the third and fourth electrodes 6(16) and 18, according to the principle of a concentration cell, due to a difference in partial pressure of the component to be measured or the component which reacts with the component to be measured between the atmosphere in the gas space 10 and the reference gas. Obviously, the solid electrolyte body 4, and the first and second electrodes 6(16), 8 constitute an electrochemical cell (pumping cell), while the solid electrolyte body 14, and the third and fourth electrodes 16(6), 18 constitute another electrochemical cell (sensing cell).

In operation of the electrochemical element arranged as described above, the electrochemical pumping action with the pumping power source 26 causing a DC current to flow between the first and second electrodes 6(16), 8, will cause a change in the concentration of the component to be measured in the atmosphere surrounding the first electrode 6(16) in the measurement-gas space 10. This change in the concentration of the gas to be measured in the atmosphere adjacent to the first electrode 6(16) is measured by the voltmeter 24 which detects an electromotive force or potential difference induced between the third electrode 16(6) and the fourth electrode 18 exposed to the external gas which serves as a reference gas. The electrochemical pumping action between the first (third) and second electrodes 6(16) and 8 is regulated so that the detected electromotive force coincides with a predetermined value.

Since the pumping current flowing through the first and second electrodes 6(16), 8 is changed with a variation in the concentration of the component to be measured in the gas in the external space 13, the concentration of the component to be measured in the external gas can be readily determined by detecting the varying pumping current with a suitable ammeter not shown.

In the arrangement of FIG. 4 described hitherto, a single common electrode is used to function not only as the inner pumping electrode (first electrode) 6 assigned to control the atmosphere in the gas space 10 by means of the electrochemical pumping action, but also as the measuring electrode (third electrode) 16 assigned to detect the controlled atmosphere within the space 10, the central part of the electrode 6(16) as the inner pumping electrode and the peripheral part of the electrode 16(6) as the measuring electrode. Consequently, the concentration of the component to be measured in the controlled atmosphere surrounding the third electrode 16(6) can be obtained as a potential difference (electromotive force) which is induced between the third electrode 16(6) and the fourth electrode 18 exposed to the reference gas, according to the principle of a concentration cell. And the partial pressure difference between the central part and the peripheral part of the electrode 6(16) is effectively reduced by the auxiliary pumping current flowing between the peripheral part of the electrode 16(6) and the second electrode 8 through the opening 17 of the insulating layer 15.

Further, the influence of resistance polarization due to an electrochemical pumping operation between the first and second electrodes 6(16) and 8 is minimized by the electrically insulating layer 15 whose round opening 17 is positioned adjacent to and concentrically with the annular first (third) electrode 6(16), so as to electrically separate or insulate the first and second solid electrolyte bodies 4, 14 from each other. Accordingly, a decrease in the accuracy of detection of the electromotive force between the third and fourth electrodes 16(6), 18 is effectively restrained by the provision of the electrically insulating layer 15.

Figure 5:
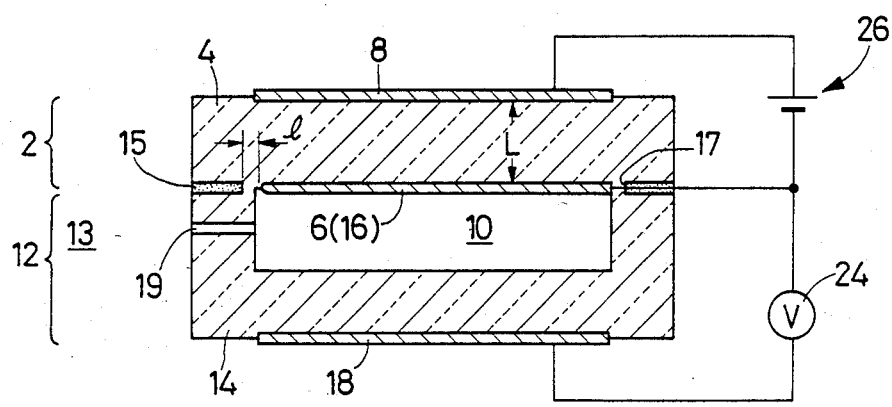

In the second basic arrangement of FIG. 5 according to the invention, the gas space 10 as an internal cavity defined by the two solid electrolyte bodies 4, 14 has a sufficiently large volume, and communicates with the external space 13 with a pin hole 19 which is formed through a portion of the second solid electrolyte body 14 at its connection with the first solid electrolyte body 4. The gas in the external space 13 is introduced through the pin hole 19 into the gas space 10, with a predetermined diffusion resistance of the pin hole 19, whereby the first (third) electrode 6(16) in the gas space 10 is exposed to the introduced gas. In the present arrangement, the electrically insulating layer 15 is disposed in the same plane as the first (third) electrode 6(16) such that the first (third) electrode 6(16) is disposed within the round opening 17, with a slight radial clearance between the periphery of the opening 17 and the outer circumference of the first (third) electrode 6(16). In other words, the round opening 17 has a diameter slightly greater than the outside diameter of the first (third) electrode 6(16). In this arrangement the peripheral part of the electrode 6(16), which is adjacent to the round opening 17 of the insulating layer 15, works as the measuring electrode (third electrode) 16. In other aspects of this arrangement, the present arrangement of FIG. 5 is identical with the arrangement of FIG. 4. The same reference numerals as used in FIG. 4 are given in FIG. 5 to identify the corresponding elements.

Figure 6:
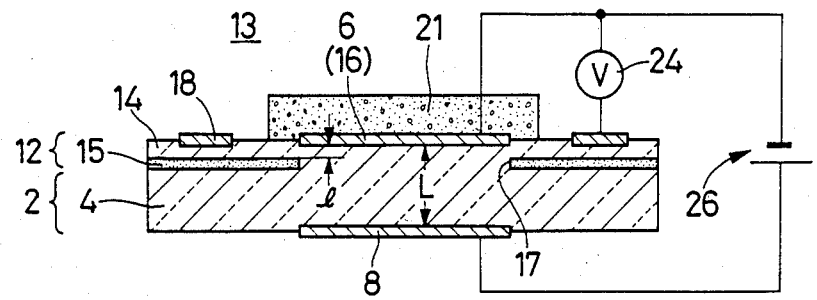

The third basic arrangement of FIG. 6 according to the invention is different from the previous two arrangements, in that the diffusion resistance means takes the form of a porous ceramic layer 21. Described more specifically, the first and second electrolyte bodies 4, 14 are provided as a single layer of solid electrolyte, and the first (third) electrode 6(16) and the second electrode 8 are disposed concentrically with each other on the opposite surfaces of the solid electrolyte layer (4, 14). The fourth electrode 18 takes the form of an annulus which has a suitable radial wall width and is disposed on the surface of the solid electrolyte layer (4, 14) on which the first (third) electrode 6(16) is disposed, such that the annular fourth electrode 18 is located radially outwardly of the first (third) electrode 6(16) with a predetermined radial clearance therebetween. The first (third) electrode 6(16) is covered with the porous ceramic layer 21 which serves as diffusion-resistance means of the present electrochemical element. This porous ceramic layer 21 has a porous structure of a suitable thickness which has a predetermined diffusion resistance to the molecules of the component to be measured in the gas. In the present arrangement, the gas in the external space 13 diffuses through the porous structure of the ceramic layer 21, with the predetermined resistance, and contacts the first (third) electrode 6(16) covered by the ceramic layer 21.

The insulating layer 15 is disposed adjacent to the first (third) electrode 6(16) such that the round opening 17 is concentric with the electrode 6(16), so as to effect partial electrical insulation between the first solid electrolyte body 4 on which the fourth electrode 18 is disposed, and the second solid electrolyte body 14 on which the second electrode 8 is disposed. The insulating layer 15 electrically insulates or separates the second electrode 8 from the fourth electrode 18.

In this arrangement of FIG. 6, too, a pumping action takes place between the first and second electrodes 6, 8, to control the concentration of the component to be measured in the atmosphere adjacent to the first electrode 6. Simultaneously, the thus controlled concentration of the component to be measured or the component which reacts with the component to be measured is detected as a potential difference between the third electrode 16, which is mainly the peripheral part of the electrode 16(6), and the fourth electrode 18 which is electrically separated from the second electrode 8. Therefore, like the first and second basic arrangements of FIGS. 4 and 5, the present basic arrangement of FIG. 6 is capable of detecting the concentration of the component to be measured in the atmosphere adjacent to the first (third) electrode 6(16) with a minimum degree of electrochemical pumping operation between the first and second electrodes 6(16), 8. Hence, the solid electrolyte body 4 is effectively protected against deterioration. Further, the insulating layer 15 is effective to prevent the resistance polarization due to the pumping action, and assure high accuracy of detection of a potential difference between the first and fourth electrodes 16(6), 18.

Figure 7:
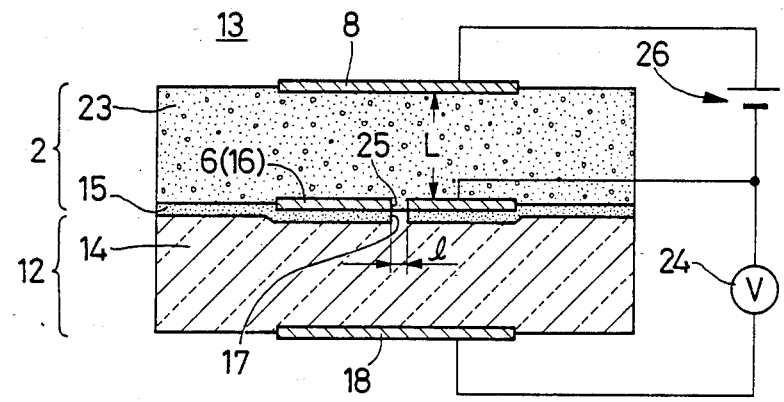

The fourth basic arrangement of FIG. 7 according to the invention is similar to the arrangement of FIG. 6 in that the diffusion-resistance means is provided in the form of a porous layer. However, the present arrangement is characterized in that the porous layer is made of a solid electrolyte material.

More specifically, reference numeral 23 indicates a porous solid electrolyte body which serves also as diffusion-resistance means having a predetermined diffusion resistance. On the opposite surfaces of this porous solid electrolyte body 23, the first (third) and second electrodes 6(16) and 8 are disposed concentrically with each other. On the surface of the porous first solid electrolyte body 23 on which the first (third) electrode 6(16) is disposed, there is formed the insulating layer 15 which has the round opening 17 with a small diameter. The second solid electrolyte body 14 cooperates with the porous first solid electrolyte body 23 to sandwich the first (third) electrode 6(16) and the insulating layer 15. On the outer surface of the second solid electrolyte body 14 remote from the insulating layer 15, there is disposed the fourth electrode 18. The first (third) electrode 6(16) has a central aperture 25 aligned with the round opening 17 of the insulating layer 15. The second solid electrolyte body 14 and the porous first solid electrolyte body 23 are electrically connected to each other at the interior of the aligned central hole and opening 17, 25, so that a potential difference between the third (first) and fourth electrodes 16(6), 18 may be detected by the voltmeter 24.

In the thus constructed arrangement of FIG. 7, the porous first solid electrolyte body 23 and the second solid electrolyte body 14 are partially electrically insulated from each other by the insulating layer 15, except at their portions within the round opining and the aperture 25. In other words, the solid electrolyte body 14 is electrically connected, through the central hole and opening 25, 17, to the portions of the porous first solid electrolyte body 23 adjacent to the inner surface of the first (third) electrode 6(16) opposite to the second electrode 8.

Figure 8:
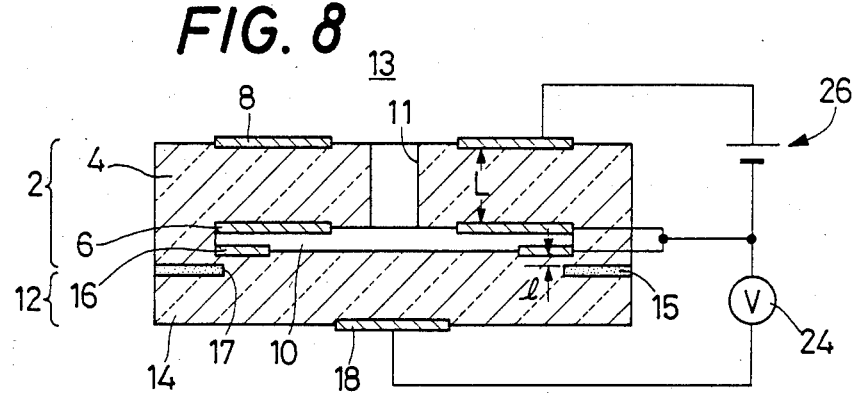

The fifth arrangement shown in FIG. 8 is a modification of the first arrangement of FIG. 4, wherein the first and third electrodes 6 and 16 are not constituted by a single common electrode, but are provided as separate electrodes which are electrically connected to each other. Although the first and third electrodes 6, 16 are electrically connected at a point outside the solid electrolyte bodies 4, 14, it is possible to connect the electrodes 6, 16 within the solid electrolyte bodies 4, 14. In this embodiment, too, the electrically insulating layer 15 is disposed such that its round opening 17 is located adjacent to the third electrode 16, whereby the two solid electrolyte bodies 4, 14 are partially electrically insulated from each other by the insulating layer 15. The third electrode 16 is mainly the central part of the electrode 16(6) which is adjacent to the round opening 17 of the insulating layer 15.

In the above arrangement, an electrochemical pumping operation occurs between the first electrodes 6(16), and the second electrode 8. Since the third electrode 6(16) and the fourth electrode 18 are electrically connected by the solid electrolyte bodies 23, 14, a potential difference between the third and first electrodes 16(6) and the fourth electrode 18 is detected by the voltmeter 24.

Because the potential of the third electrodes 16(6) which undergo the pumping operation is directly detected, the pumping action will not be conducted in an excessive degree. Therefore, no deterioration of the solid electrolyte bodies 4, 14 will result. Further, the measurement of the potential difference will not be significantly influenced by the resistance polarization due to the electrochemical pumping operation, since the pumping and sensing cells are electrically insulated from each other by the insulating layer 15, except at their portions adjacent to the third electrode 16. This means improved accuracy of measurement of the potential difference between the third electrodes 16(6) and the fourth electrode 18.

In the electrochemical element which has been described in its various preferred forms, the ion-conductive solid electrolyte bodies (4, 14) of the pumping and sensing cells are made of oxygen-ion conductive materials such as zirconia ceramics and solid solutions of $Bi_2O_3$—$Y_2O_3$, proton-conductive materials such as $SrCe_{0.95}Yb_{0.05}O_{3-\alpha}$, or halogen-ion conductive materials such as $CaF_2$. While each solid electrolyte body usually has a planar or sheet-like shape, it may take other suitable shapes. Preferably, the solid electrolyte body 4, 14 is prepared by stacking a plurality of green sheets into a laminar structure and firing the green laminar structure into a unitary or integral body.

The first, second and third electrodes 6, 8, 16 formed on the solid electrolyte body (4, 14) are preferably porous structures which are formed of a material whose major component is selected from the platinum group which comprises platinum, palladium, rhodium, iridium, ruthenium and osmium. The fourth electrode 18 is formed of the same material as the first, second and third electrodes 6, 8, 16, or may be made of a mixture of nickel and nickel oxide, which gives a reference oxygen partial pressure. The electrodes are formed on the appropriate places of the solid electrolyte bodies, either by co-firing the green layers of the electrodes together with the green sheets of the solid electrolyte bodies, or by way of applying the electrode material to the surfaces of the fired solid electrolyte bodies by sputtering, plating, paste-baking or other suitable technique. The configuration and dimensions of the electrodes are determined as needed, depending upon the specific form of the diffusion-resistance means, and other factors.

As previously described referring to FIGS. 4, 5 and 8, the first electrode 6 of the pumping cell 2 and the third electrode 16 of the sensing cell 12 are preferably disposed within an internal cavity (10) formed in the electrochemical element, so that these electrodes 6, 16 are exposed to the gas which is introduced from the external space into the cavity through suitable diffusion-resistance means as previously described.

The internal cavity (10) may be designed to function as diffusion-resistance means and communicate with the external space 13 in which the gas to be measured exists. If necessary, the internal cavity (10) may be filled with a porous structure which has a lower diffusion resistance than the diffusion-resistance means. In this case, the porous structure filling the cavity (10) is preferably adapted such that a portion of the porous structure layer covering the third electrode (measuring electrode) 16 has a lower porosity, namely, a higher diffusion resistance, than a portion of the porous structure covering the first electrode (inner pumping electrode) 6. This makes it possible to effect an auxiliary pumping operation between the two electrodes namely the third electrode and the other electrode with a reduced amount of auxiliary pumping current. Consequently, a difference in partial pressure of the component to be measured between the atmospheres adjacent to the first and third electrodes 6, 16 can be reduced, with a result of minimizing an influence of resistance polarization due to the auxiliary pumping, on the output of the sensing cell 12.

Alternatively, at least one of the first solid electrolyte body 4 of the pumping cell 2 and the second solid electrolyte body 14 of the sensing cell 12 may be a porous structure which serves as diffusion-resistance means having a predetermined diffusion resistance.

Further, the first and second solid electrolyte bodies 4, 14 are electrically insulated or separated at least partially from each other by electrically resistant means, according to the principle of the invention. Generally, this electrically resistant means is provided in the form of an electrically insulating layer (15), whose configuration, dimensions and location in the solid electrolyte bodies may be selected as needed, so as to effect at least partial electrical insulation between the two solid electrolyte bodies 4, 14. The electrically resistant means (15) is not required to provide perfect electrical insulation. The required insulating property of the electrically resistant means (15) depends upon various factors such as the location of the electrodes. More particularly, the electrically resistant means (15) is required to have an electrical resistance which is higher than that of the solid electrolyte body, to such an extent that is sufficient to achieve a desired degree of reduction of the influence of the resistance polarization which is caused by the electrochemical pumping operation between the first and second electrodes 6, 8. Generally, the electrically resistant means (15) is made of electrically insulating ceramic materials such as alumina, or other highly electrically resistive ceramics as disclosed in Japanese Patent Application laid open in 1984 under Publication No. 59-131574.

As previously indicated, the insulating layer 15 is dimensioned and positioned so that its inner circumference 17 is located adjacent to the first (third) electrode 6(16). It is preferred that the width of the opening of the electrically resistant means, i.e., a distance l between the insulating layer 15 and the first (third) electrode 6(16) is less than one half ($\frac{1}{2}$) of a distance L between the first (third) and second electrodes 6(16), 8, as indicated in FIGS. 4, 6, 7 and 8. More preferably, the distance l is less than one fifth (1/5) of the distance L. For example, if the distance l is one half of the distance L, the influence of the resistance polarization due to a pumping action is reduced to about one half of that which would be present if the insulating layer (15) is not provided. In summary, the principle of the present invention requires that the electrically resistant means (15) be located as close as possible to the first (third) electrode 6(16) in the direction of thickness of the electrode, for minimizing the influence of the resistance polarization to assure precise or accurate determination of the measurement component by the electrochemical element.

As indicated in FIGS. 4, 7 and 8, it is preferred that the round opening 17 of the insulating layer 15 is located adjacent to a portion of the first electrode 6 at which the diffusion resistance to the component to be measured of the gas from the external space 13 is maximum. This arrangement makes it possible to detect a potential difference between the third and fourth electrodes 16, 18, which corresponds to the lowest partial pressure of the component to be measured adjacent to the first electrode 6. Since the pumping operation between the first and second electrodes 6, 8 is controlled based on such a low partial pressure, the first solid electrolyte body 4 is effectively protected against deterioration at its portion contacting the first electrode 6.

In the electrochemical element according to the invention, the ambient air may be suitably used as a reference gas to which the fourth electrode 18 is exposed. In one preferred form of this arrangement, the second solid electrolyte body 14 may be formed with an internal reference-gas space (air passage) which communicates with an external space in which the ambient air exists.

For accurate and reliable operation of the electrochemical element or device according to the invention, it is also preferred to form a heater layer on the first or second solid electrolyte body 4, 14, for holding the solid electrolyte bodies 4, 14 at a suitable operating temperature.

While the present invention has been described in its several basic arrangements and constructions, the concept of the invention will be further clarified referring to FIGS. 11-29 which show detailed constructions of an electrochemical element suitable for practicing the principle of the invention in its preferred forms. It is to be understood that these arrangements are shown and described for illustrative purpose only, and for easy understanding of the invention, and that the invention is by no means limited to the details of the following disclosure.

Figure 11:
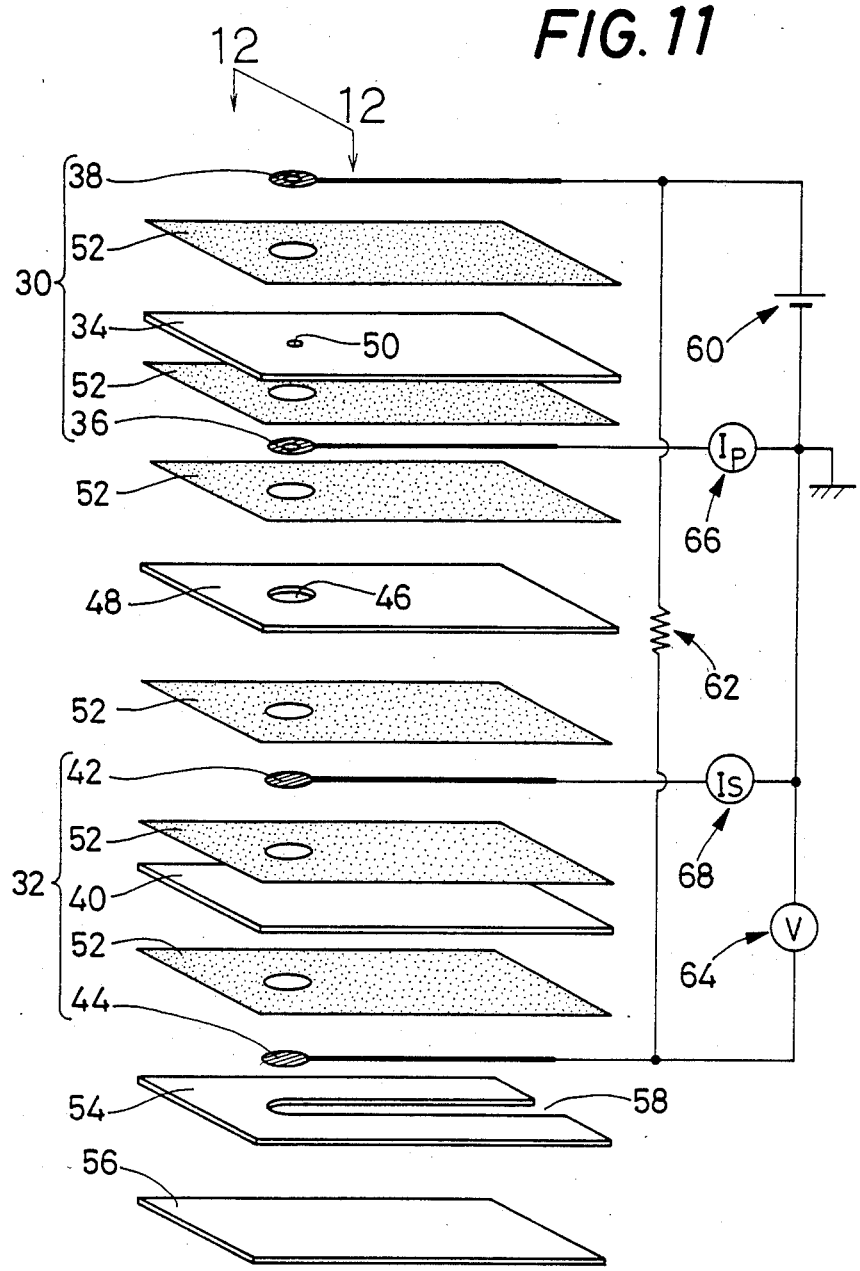
FIG. 11 is an exploded illustration in perspective of one form of an electrochemical element according to the invention, showing an example of an electrical arrangement for measurement according to the invention.
Figure 12:
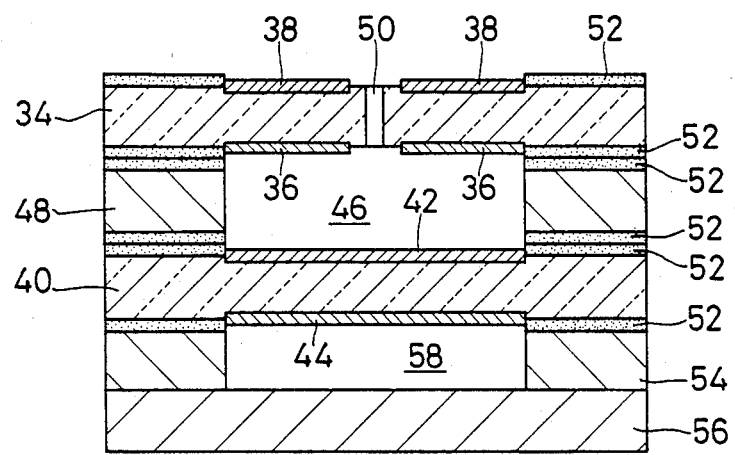
FIG. 12 is a cross sectional view taken along line 12—12 of FIG. 11.

Referring to FIGS. 11 and 12, there is shown one form of an oxygen sensor for determining the concentration of oxygen in a gas, incorporating an electrochemical element of a laminar structure which comprises planar solid electrolyte bodies, and employs an electrical arrangement for applying an auxiliary pumping current, as illustrated in FIG. 1. The electrochemical element comprises an electrochemical pumping cell 30 and an electrochemical sensing cell 32 superposed on the pumping cell 30.

The electrochemical pumping cell 30 comprises a first planar solid electrolyte body 34 made of zirconia or other ceramics, and an annular porous inner pumping electrode (first electrode) 36 and an annular porous outer pumping electrode (second electrode) 38 which are made of platinum or other conductive materials. The inner and outer pumping electrodes are disposed concentrically with each other on opposite sides of the first solid electrolyte body 34. Similarly, the electrochemical sensing cell 32 comprises a second planar solid electrolyte body 40, and an annular porous measuring electrode (third electrode) 42 and an annular porous reference electrode (fourth electrode) 44 which are disposed concentrically with each other on the opposite sides of the second solid electrolyte body 40. Between the pumping and sensing cells 30, 32, there is interposed a gas-tight ceramic layer 48 which has a hole serving to define an internal cavity 46.

Described more precisely, the internal cavity 46 is defined by the gas-tight ceramic layer 48, inner pumping electrode 36 and measuring electrode 42, as shown in FIG. 12, when the pumping and sensing cells 30, 32 are superposed on each other with the gas-tight ceramic layer 48 sandwiched therebetween. In other words, the inner pumping electrode 36 of the pumping cell 30 and the measuring electrode 42 of the sensing cell 32 are exposed to the internal cavity 46 such that the two electrodes face each other. The first solid electrolyte body 34 is formed with a pin hole 50 through which the internal cavity 46 communicates with an external space in which the gas to be measured exists. The pin hole 50 functions as diffusion-resistance means having a predetermined diffusion resistance, and permits the gas to be introduced into the internal cavity 46 with the predetermined diffusion resistance.

Four insulating layers 52 are provided to electrically insulate electrical leads of the respective electrodes of the pumping and sensing cells 30, 32. The outer pumping electrode 38 of the pumping cell 30 is exposed to the external gas, while the reference electrode 44 of the sensing cell 32 is disposed in an air passage 58 which is defined by gas-tight ceramic layers 54, 56 superposed on each other. The ambient air is introduced into the air passage 58 through an inlet at its one end, whereby the reference electrode 44 is exposed to the ambient air in the air-passage 58.

For applying a primary pumping current to the pumping cell 30 of the electrochemical element thus constructed, a pumping power source (DC power source) 60 is connected to the pumping electrodes 36, 38. This power source 60 is also connected via a resistor 62 to a circuit which includes the measuring and reference electrodes 42, 44 of the sensing cell 32. The power source 60 causes a primary pumping current to flow through the two pumping electrodes 36, 38 of the pumping cell 30, while at the same time causing an auxiliary pumping current to flow through the measuring and reference electrodes 42, 44 of the sensing cell 32, to effect an intended auxiliary pumping action between the electrodes 42, 44.

A voltmeter 64 is connected to the meauring and reference electrodes 42, 44 of the sensing cell 32, to detect an electromotive force (potential difference) between these two electrodes 42, 44. Meanwhile, a first ammeter 66 is provided to detect a pumping current passing through the outer pumping electrode 36 (first electrode) of the pumping cell 30, while a second ammeter 68 is provided to detect an auxiliary pumping current passing through the measuring electrode 42 (third electrode) of the sensing cell 32. A sum of the primary pumping current and the auxiliary pumping current detected by the two ammeters 66, 68 is obtained as an output upon which the concentration of the component to be measured in the gas is determined.

The oxygen sensor of FIGS. 11 and 12 was tested in the ambient air (gas to be measured). The DC current applied to the pumping cell 30 by the power source 60 was controlled so that an electromotive force induced on the sensing cell 32 (reading of the voltmeter 64) was held at 0.45 V. At this time, the primary pumping current Ip detected by the first ammeter 66 was 10.0 mA, while the auxiliary pumping current Is detected by the second ammeter 66 was 0.1 mA. The resistance of the resistor 62 was 30KΩ.

The operation of the instant sensor of FIGS. 11 and 12 in the ambient air was continued for ten hours in the above-indicated conditions. In the meantime, a conventional oxygen sensor without an arrangement for application of an auxiliary pumping current Is was tested in the same conditions as the instant oxygen sensor. The test showed a change in the appearance of the pumping cell of the conventional oxygen sensor, and deterioration of zirconia solid electrolyte of the pumping cell. However, the instant oxygen sensor operated with an auxiliary pumping current Is of 0.1 mA demonstrated no change in its appearance. Thus, the test revealed sufficient durability of the instant oxygen sensor under an atmoshphere (gas to be measured) having a high oxygen concentration.

Figure 14:
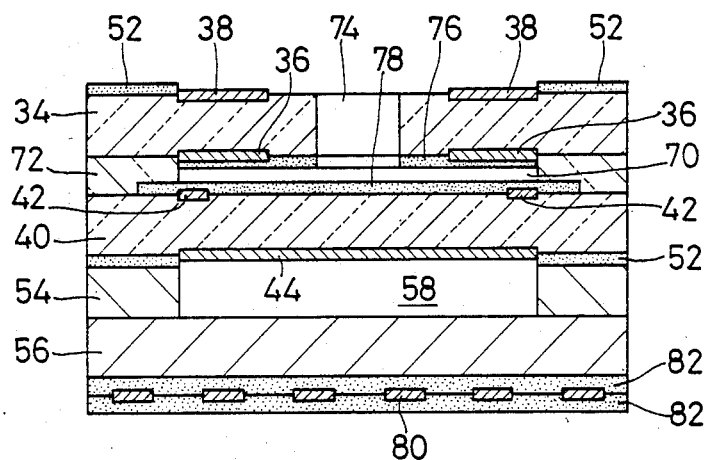
FIG. 14 is a cross sectional view taken along line 14—14 of FIG. 13.
Figure 13:
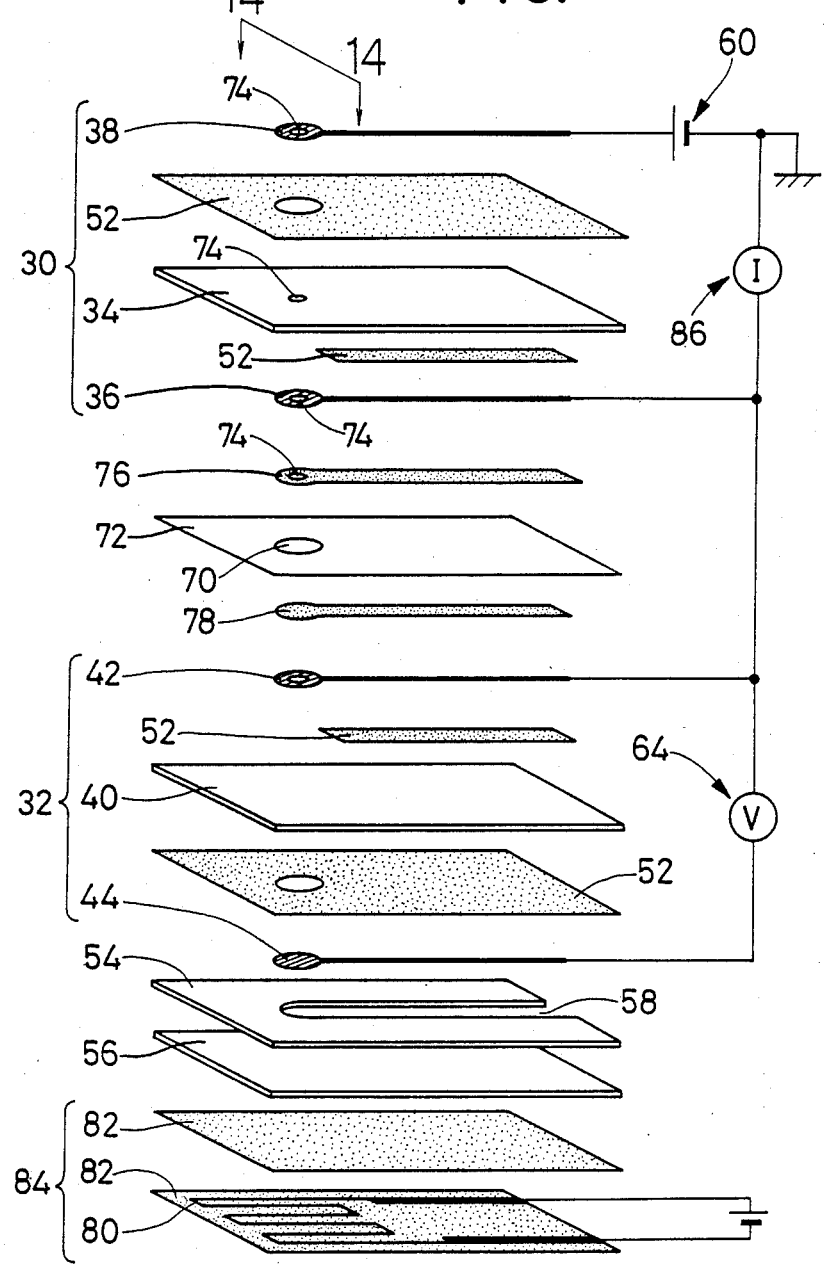
FIG. 13 is a view corresponding to FIG. 11, showing a modified embodiment of the invention.

FIGS. 13 and 14 show a modified arrangement of the electrochemical element, in which the internal cavity in the form of an annular thin flat space 70 formed between the pumping and sensing cells 30, 32 serves as diffusion-resistance means, unlike the internal cavity 46 of the preceding arrangement of FIGS. 11 and 12. The flat space 70 is formed in a spacer layer 72 of a solid electrolyte material interposed between the pumping and sensing cells 30, 32. The first solid electrolyte body 34 of the pumping cell 30 has an aperture 74 through which the gas in the external space is introduced into the thin flat space 70.

A porous insulating strip 76 is disposed between the inner pumping electrode 36 of the pumping cell 30 and the spacer layer 72, while another porous insulating strip 78 is disposed between the measuring electrode 42 of the sensing cell 32 and the spacer layer 72. Therefore, the inner pumping and measuring electrodes 36, 42 are exposed through the porous insulating strips 76, 78 to the gas which has diffused to the radially outer portion of the thin flat space 70. The diffusion resistances of the porous insulating strips 76, 78 are much lower than that of the diffusion-resistance means in the form of the thin flat space 70. However, the porosity of the porous insulating strip 78 covering the measuring electrode 42 is selected to be lower than that of the porous insulating strip 76 covering the inner pumping electrode 36. That is, the insulating strip 78 has a higher diffusion resistance than the insulating strip 76, so that an amount of auxiliary pumping current flowing through the electrodes 36, 42 is held relatively small, to reduce a difference in the partial pressure of the component to be measured in the atmospheres adjacent to the two electrodes 36, 42, i.e., to reduce an electromotive force induced between the electrodes according to the principle of a concentration cell. The width of the porous insulating strip 76 is selected to be substantially the same as the outside diameter of the inner pumping electrode 36, while the width of the porous insulating strip 78 is selected to be only slightly larger than the outside diameter of the measuring electrode 42. With the strips 76, 78 thus dimensioned, the first and second solid electrolyte bodies 34, 40 of the pumping and sensing cells 30, 32 are electrically connected by the solid electrolyte of the spacer layer 72.

The electrochemical element described above is provided with an electrical heater 84 for heating the pumping and sensing cells to a suitable operating temperature, so as to assure accurate and reliable operation of the electrochemical element. The heater 84 is disposed on the outer side of the sensing cell 32, and comprises a heating element 80 which is formed between two insulating layers 82, 82.

The voltmeter 64 is provided to detect an electromotive force induced between the measuring and reference electrodes 42, 44 of the sensing cell 32, while the pumping power source 60 is provided to apply a pumping current between the two pumping electrodes 36, 38 of the pumping cell 30. An ammeter 86 is provided to measure a sum of the primary pumping current passing through the inner pumping electrode 36 of the pumping cell 30, and the auxiliary pumping current passing through the measuring electrode 42 of the sensing cell 32.

In the oxygen sensor constructed as described hitherto wherein the first and second solid electrolyte bodies 34, 40 of the pumping and sensing cells 30, 32 are electrically connected to each other by the solid electrolyte spacer layer 72, a part of the primary pumping current flowing through the pumping electrodes 36, 38 is permitted to flow from the outer pumping electrode 38 toward the measuring electrode 42 or vice versa, whereby an effective auxiliary pumping is effected. In this sense, the instant arrangement for application of an auxiliary pumping current corresponds to the basic arrangement illustrated in FIG. 3.

As indicated above, the instant oxygen sensor is adapted to utilize a part of the primary pumping current used for the pumping cell 30, as an auxiliary pumping current which flows through the measuring electrode 42 of the sensing cell 32. The amount of the auxiliary pumping current should be determined depending upon the size of a portion of the porous insulating strip 78 covering the measuring electrode 42. Namely, if that portion of the strip 78 has a round shape, the amount of a leak current from the pumping cell 30 (i.e., auxiliary pumping current) can be adjusted by increasing or reducing the diameter of the round portion of the strip 78 covering the electrode 42. The auxiliary pumping action causes a considerable decrease in difference in the oxygen partial pressure between the atmospheres adjacent to the inner pumping electrode 36 and the measuring electrode 42.

Figure 15:
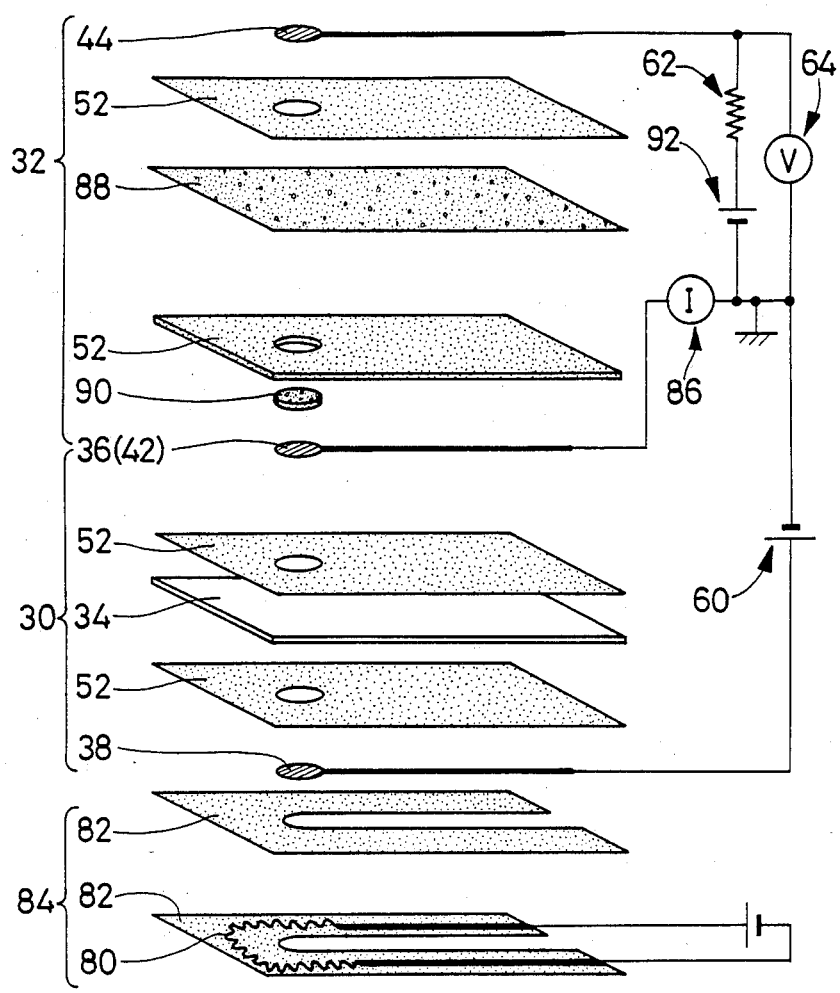
FIGS. 15 and 16 are views corresponding to FIG. 11, illustrating other modified embodiments of the invention, respectively.

FIG. 15 shows another arrangement of an electrochemical element which is different in some aspects from the preceding arrangements of FIGS. 11 and 13. More specifically, the heater 84 is formed on the outer side of the pumping cell 30, and the sensing cell 32 uses a porous solid electrolyte body 88 which functions as diffusion-resistance means having a predetermined diffusion resistance. Another difference lies in that a single common electrode serves as the first and third electrodes 36, 42. Further, a round opening in the insulating layer 52 is filled with a porous solid electrolyte filler 90 whose diffusion resistance is far lower than that of the porous solid electrolyte body 88. The influence of the solid electrolyte filler 90 on the rate of diffusion of the component to be measured toward the common electrode 36(42) is negligible. The upper surface of the common electrode 36(42) contacts the porous solid electrolye filler 90 and serves as the measuring electrode, while the lower surface of the common electrode 36(42) contacts the first solid electrolyte body 34 and serves as the inner pumping electrode.

In the present arrangement, the reference electrode 44 of the sensing cell 32 is exposed to the gas to be measured (which is used as a reference gas) in the external space. An auxiliary pumping power source 92 (DC power source) is connected between the reference and measuring electrodes 44, 42(36), to apply an auxiliary pumping current to these electrodes 44, 42(36).

Upon application of a primary pumping current by the power source 60 between the two pumping electrodes, i.e., between the outer pumping electrode 38 and the inner pumping electrode 36(42), the gas diffuses through the reference electrode 44 and the porous solid electrolyte body 88 of the sensing cell 32, with a predetermined diffusion resistance. The gas is thus retained in the porous structure of the porous solid electrolyte filler 90. Meanwhile, an auxiliary pumping current is applied by the power source 92 between the reference electrode 44 and the upper surface of the common electrode 42(36), i.e., the measuring electrode 42, whereby the atmosphere adjacent to the upper surface of the common electrode 36(42) is controlled so as to reduce a difference in the partial pressure of the component to be measured between the atmospheres adjacent to the upper and lower surfaces of the common electrode, i.e., measuring and inner pumping electrodes 42, 36. Thus, the application of an auxiliary pumping current contributes to effective reduction in an electromotive force induced due to such a partial pressure difference according to the principle of a concentration cell.

Figure 16:
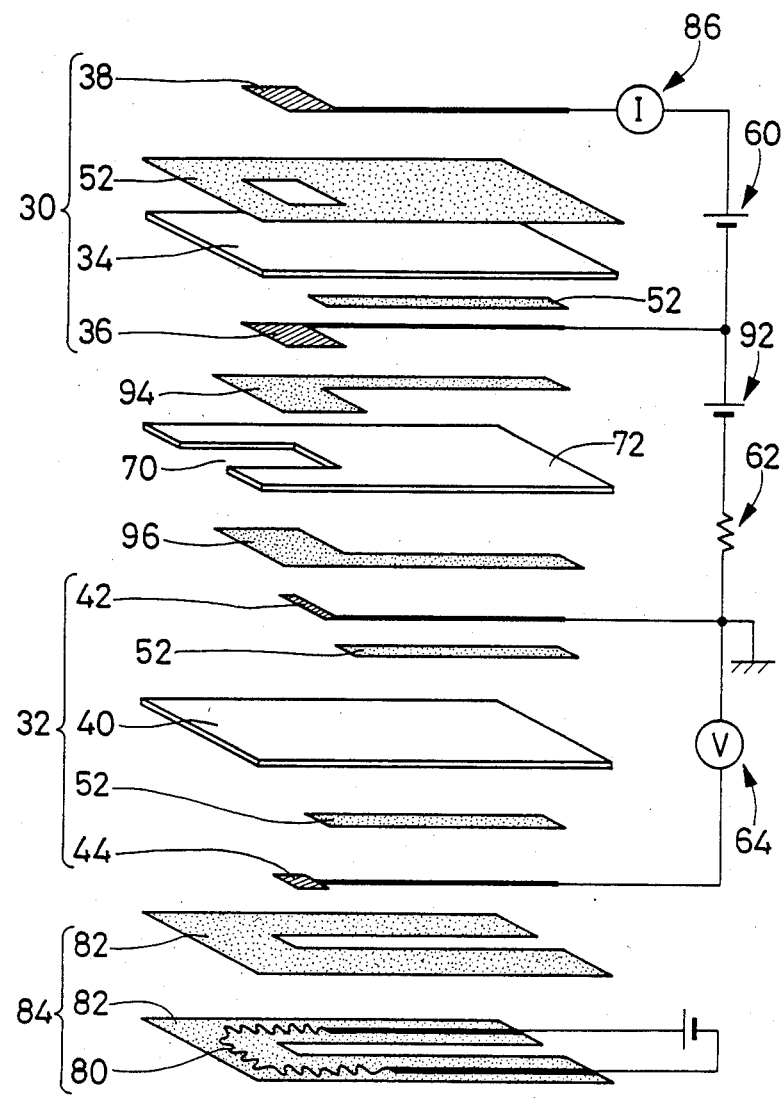

An electrochemical element shown in FIG. 16 is characterized by the thin flat space 70 (diffusion-resistance means) having a rectangular shape which is open at its one side corresponding to one end of the electrochemical element, so that the gas is directly introduced into the flat space 70. This rectangular thin flat space 70 is formed in the spacer layer 72 which is interposed between the pumping and sensing cells 30, 32. The inner pumping electrode 36 of the pumping cell 30 and the measuring electrode 42 of the sensing cell 30 are exposed to the gas in the thin flat space 70, via porous insulating strips 94, 96 which have a very low diffusion resistance.

The auxiliary pumping power source 92 is connected in a circuit which incorporates the inner pumping and measuring electrodes 36, 42 of the pumping and sensing cells 30, 32. In this arrangement, an auxiliary pumping current is applied so as to flow through these electrodes 36, 42, according to the method illustrated in FIG. 2. The first and second electrolyte bodies 34, 40 of the pumping and sensing cells 30, 32 are electrically connected to each other by the spacer layer 72, so that the auxiliary pumping current may flow between the electrodes 36, 42 through opposite portions of the spacer layer 72 which define the opposite sides of the rectangular thin flat space 70.

Figure 17:
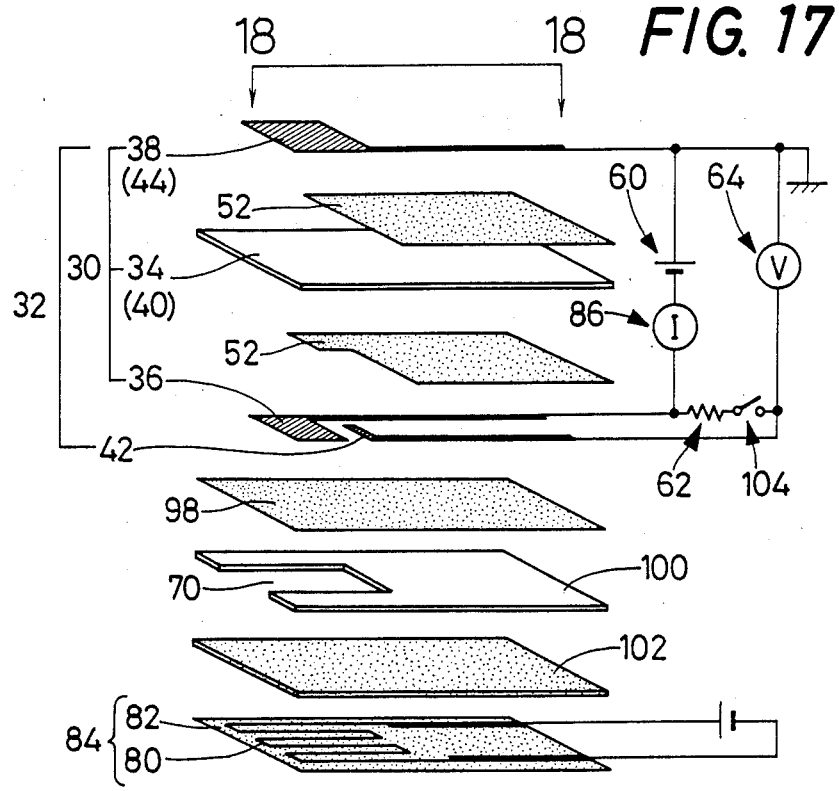
FIG. 17 is a view corresponding to FIG. 11, illustrating a further modified embodiment of the invention.
Figure 18:
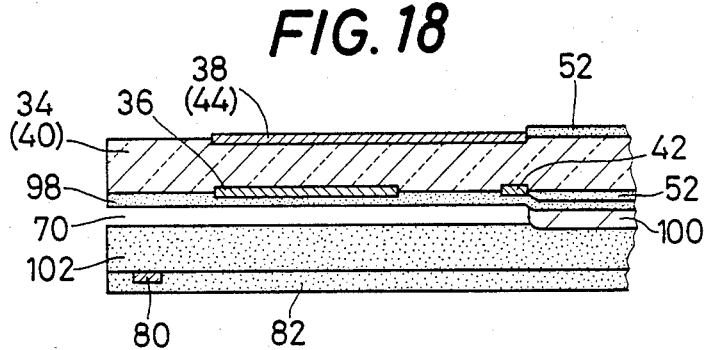
FIG. 18 is a view in cross section taken along line 18—18 of FIG. 17.

In a further modified form of an electrochemical element illustrated in FIGS. 17 and 18, the pumping and sensing cells 30, 32 use a single common solid electrolyte body 34(40), and a single common electrode which serves as the outer pumping electrode 38 of the pumping cell 30, and the reference electrode 44 of the sensing cell 32. Like the preceding arrangement of FIG. 16, the present arrangement has a rectangular thin flat space 70.

This flat space 70, however, is defined by a gas-tight ceramic layer 100 and a gas-tight insulating layer 102. The electrical heater 84 is formed on the outer surface of the gas-tight insulating layer 102.

The inner pumping electrode 36 of the pumping cell 30 and the measuring electrode 42 of the sensing cell 32 are electrically connected to each other through the resistor 62 and a switch 104, so that a part of a primary pumping current for the pumping cell 30 may be used as an auxiliary pumping current to be applied between the measuring and reference electrodes 42, 44 of the sensing cell 32. Described in more detail, the switch 104 connected to the resistor 62 is turned on and off according to the operating condition of the electrochemical element. The auxiliary pumping current is applied to the measuring and reference electrodes 42, 44 while the switch 104 is held on. The auxiliary pumping action with the switch 104 held on will make it possible to reduce a difference in oxygen partial pressure in the atmospheres adjacent to the inner pumping electrode 36 and the measuring electrode 42, even if the gas to be measured is the ambient air or other atmosphere having a high oxygen concentration. Hence, the solid electrolyte body 34 of the pumping cell 30 may be effectively protected against otherwise possible deterioration.

Figure 19:
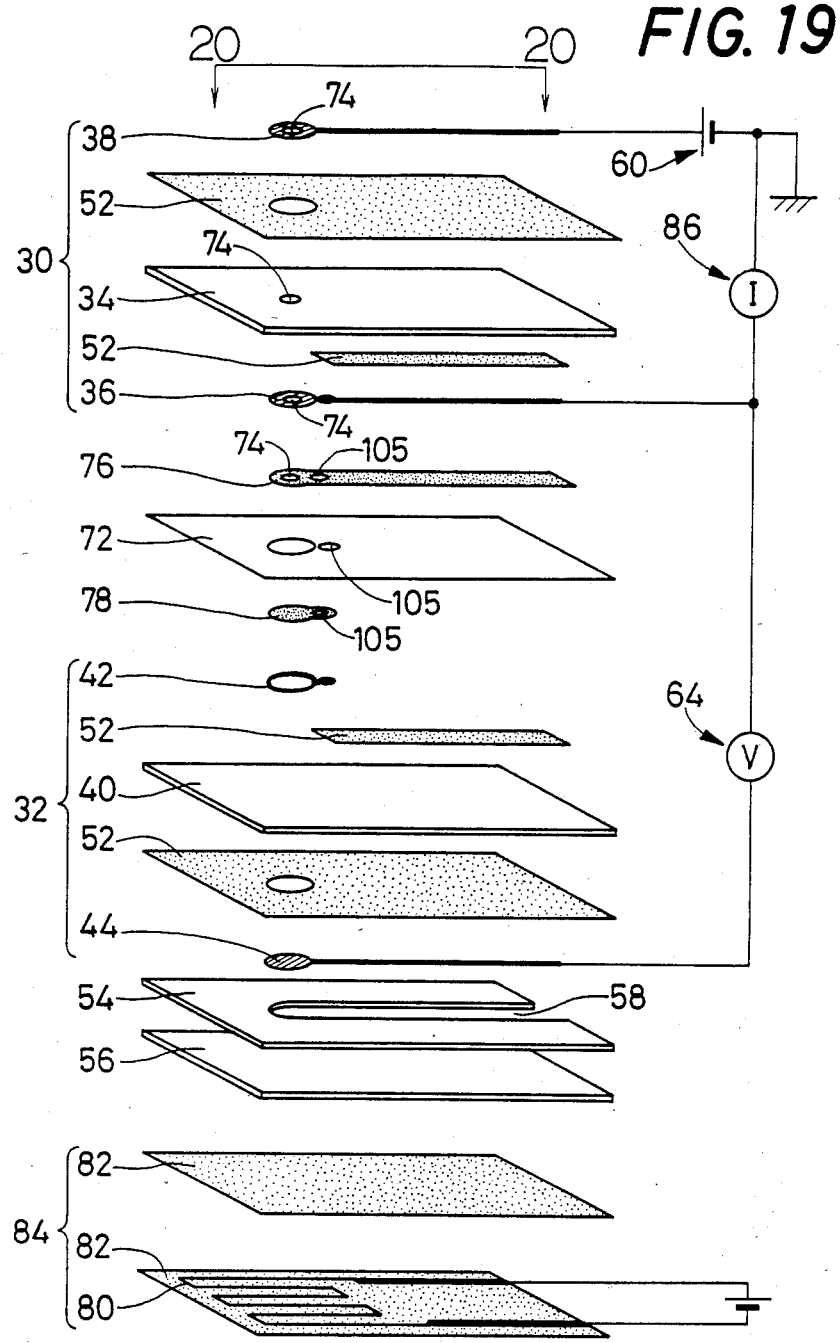
FIG. 19 is a view corresponding to FIG. 11, showing a still further embodiment of the invention.
Figure 20:
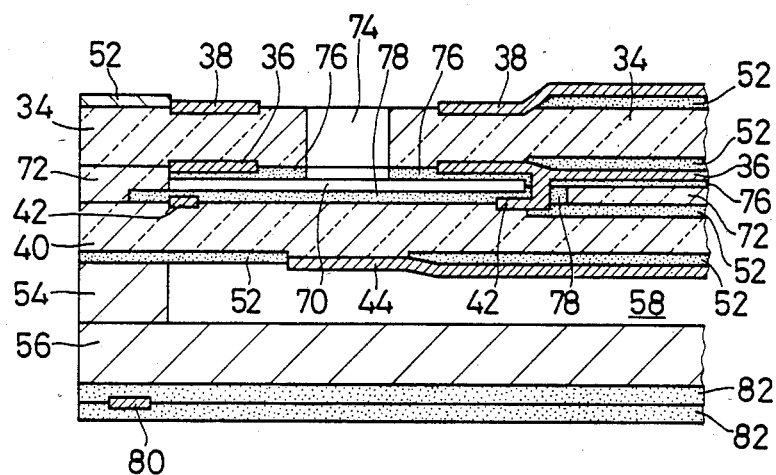
FIG. 20 is a cross sectional view taken along line 20—20 of FIG. 19.

FIGS. 19 and 20 illustrate a further modified arrangement of an electrochemical element of the present invention, wherein the inner puming electrode 36 (first electrode) and the measuring electrode 42 (third electrode) are electrically connected to each other by their lugs accommodated in a pin hole 105 which is formed through the porous insulating members 76, 78 and the solid electrolyte spacer layer 72. The first and second solid electrolyte bodies 34 and 40 are electrically connected to each other by the solid electrolyte spacer layer 72. The primary pumping power source 60 is connected between the mutually connected electrodes 36, 42, and the outer pumping electrode 38 (second electrode). While a major portion of a pumping current is applied to the inner and outer pumping electrodes 36, 38, a portion of the pumping current leaks through the solid electrolyte spacer layer 72, and flows through the measuring electrode 42. The ratio of this leakage flow through the measuring electrode 42 to the entire amount of the pumping current may be adjusted as desired, by changing the surface area of the porous insulating member 78, and thereby changing the area of contact between the solid electrolyte spacer layer 72 and the solid electrolyte body 40.

Figure 22:
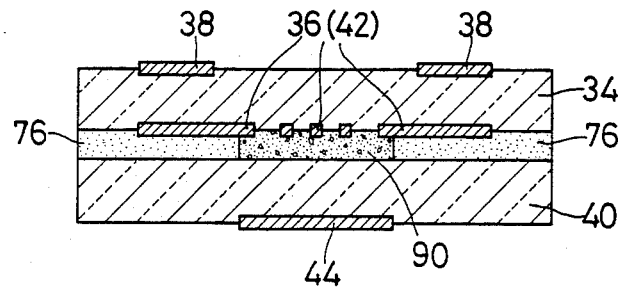
FIG. 22 is a cross sectional view taken along line 22—22 of FIG. 21.
Figure 21:
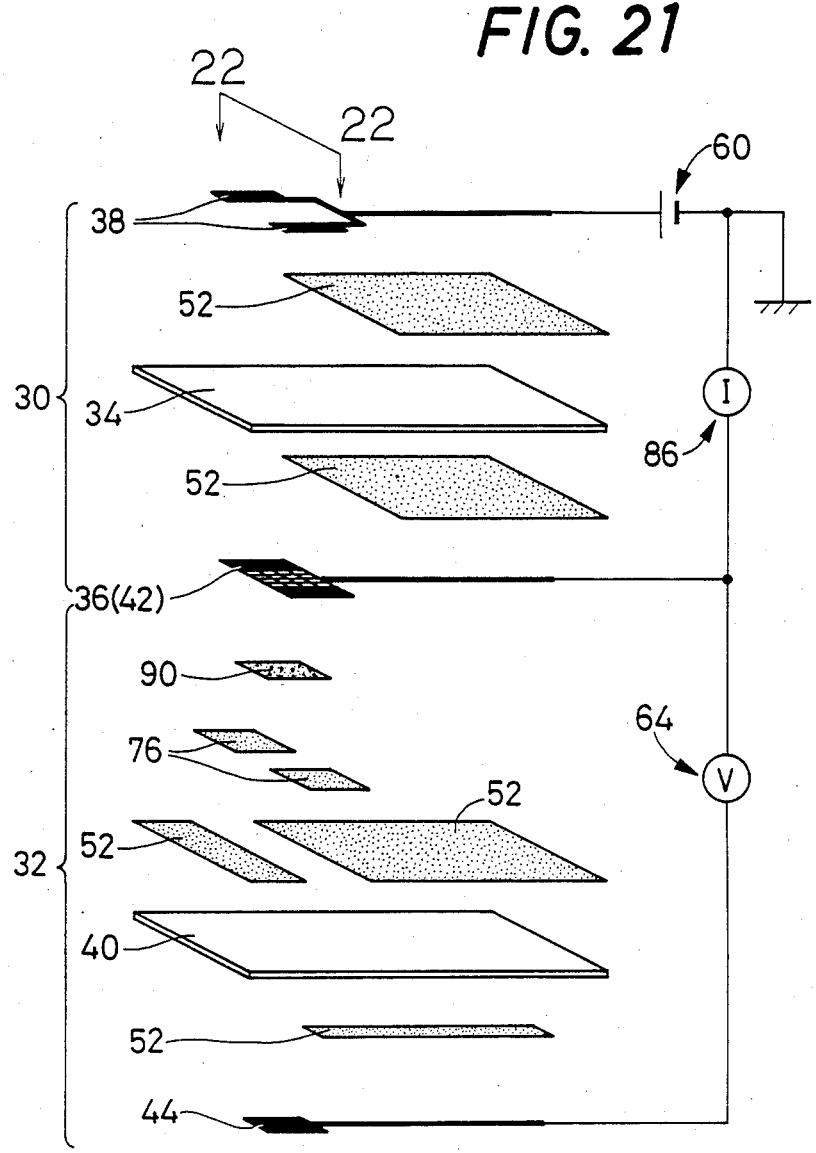
FIG. 21 is a view corresponding to FIG. 11, showing another embodiment of the invention.

In a yet further modified arrangement shown in FIGS. 21 and 22, the first and third electrodes 36, 42 are provided in the form of a single common electrode 36(42). Described in greater detail, the first or inner pumping electrode is constituted by the upper surface of the common electrode contacting the solid electrolyte body 34, primarily by the opposite end portions of the common electrode corresponding to the pair of outer pumping electrodes 38 connected to each other. On the other hand, the third or measuring electrode is constituted by the lower surface of the common electrode, more precisely, by a central portion of the common electrode contacting the porous solid electrolyte filler 90. The central portion of the common electrode 36(42) is formed as a grid, which electrically connects the solid electrolyte body 34 and the porous solid electrolyte filler 90. The filler 90 has a relatively high porosity, and a lower diffusion resistance than the porous insulating layers 76, 76.

The power source 60 is connected between the outer pumping electrode 38 and the common electrode 36(42), to apply a pumping current between the outer pumping electrodes 38, and the corresponding end portions of the common electrode 36(42). The current density on the common electrode is particularly high near the lateral edges of the electrochemical element, and low at the central grid portion. That is, a small amount of auxiliary pumping current flows through the central grid portion of the common electrode which serves as the measuring electrode 42. Thus, an auxiliary pumping operation is properly effected to reduce a difference in the partial pressure of the component to be measured between the atmospheres adjacent to the upper and lower surfaces of the common electrode 36(42).

To further illustrate the third embodiment of the method of the invention shown in FIG. 3, some embodiments of the electrochemical device of the invention will be described.

Figure 23:
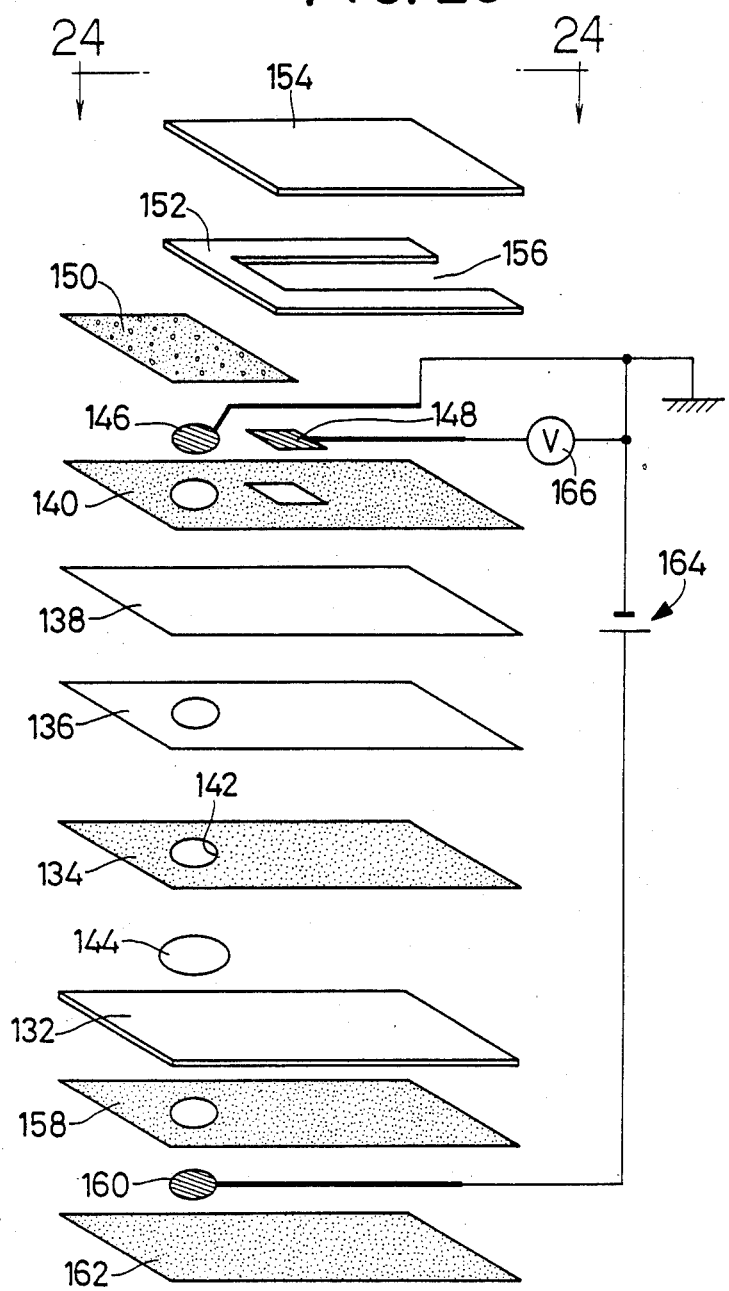
FIG. 23 is an exploded perspective view of yet another embodiment of an electrochemical element of the invention.
Figure 24:
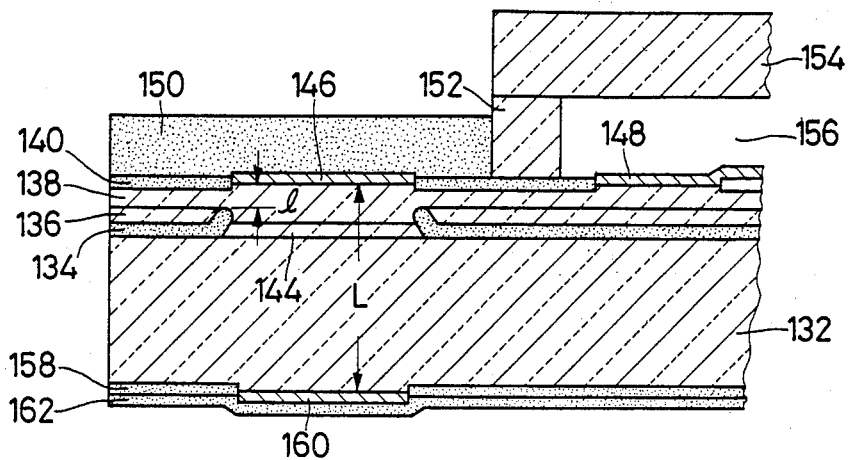
FIG. 24 is a view in cross section taken along line 24—24 of FIG. 23.

An oxygen sensor shown in FIGS. 23 and 24 is an example of an electrochemical device of a laminar structure with solid electrolyte layers, which is constructed according to the basic arrangement of FIG. 6, for determining the oxygen concentration of a gas.

In the figures, reference numeral 132 designates a solid electrolyte layer made of zirconia or similar ceramics. On this solid electrolyte layer 132, there is formed a laminar stack which consists of an electrically insulating layer 134 (made of alumina or similar insulating material), solid electrolyte layers 136, 138, and an electrically insulating layer 140 for insulating leads of a first and a fourth electrode 146, 148. The insulating layer 134 has a round opening 142 which accommodates a round solid electrolyte filler 144. Since the diameter of the filler 144 is slightly larger than the initial diameter of the round opening 142, an annular portion of the insulating layer 134 defining the periphery of the round opening 142 is bent upward toward the insulating layer 140, as illustrated in FIG. 24, while the round filler 144 rests on the solid electrolyte layer 132. The solid electrolyte layers 132, 136, 138 and the round filler 144 constitute a unitary laminar structure of solid electrolyte.

The insulating layer 140 has a round and a rectangular opening in which the first and fourth electrodes 146, 148 are accommodated, respectively, in contact with the solid electrolyte layer 138. The round first electrode 146 functions also as a third electrode. This common electrode 146 is covered by a porous ceramic layer 150 made of alumina or other ceramics. On the insulating layer 140, there are further formed a spacer member 152 and a covering member 154, which are formed of zirconia or other suitable ceramics. The spacer member 152 has a slot which serves as an air passage 156. The rectangular fourth electrode 148 indicated above is positioned so that it is exposed to an ambient air introduced as a reference gas in the air passage 156. As indicated in FIG. 23, the air passage 156 is open to the atmosphere at its right-hand side end.

On the side of the solid electrolyte layer 132 remote from the insulating layer 134, there is formed an insulating layer 158 which has a round opening accommodating a second electrode 160. This second electrode 160 is sandwiched between the solid electrolyte layer 132, and a porous protective layer 162 which covers the insulating layer 158 and the second electrode 160. An electrical lead 160 is electrically insulated between the layers 158 and 162.

In the electrochemical device constructed as described above, the insulating layer 134 divides the laminar solid electrolyte body which consists of the solid electrolyte layer 132, solid electrolyte filler 144, and solid electrolyte layers 136, 138. In other words, the insulating layer 134 electrically separates or insulates the solid electrolyte layer and filler 132, 144, from the solid electrolyte layers 136, 138. Further, the circumferential portion of the insulating layer 134 which defines the round opening 142, is upraised toward the first electrode 146 by the solid electrolyte filler 144 received in the round opening 142.

With a primary pumping current applied by the power source 164 to the first and second electrodes 146, 160, an electrochemical pumping operation is effected between these electrodes 146, 160, thereby controlling the atmosphere surrounding the first electrode 146, which has diffused through the porous ceramic layer 150 provided to function as diffusion-resistance means having a predetermined diffusion resistance. A voltmeter 166 is connected to the first electrode 146, and to the fourth electrode 148 exposed to the ambient air as a reference gas. To determine the oxygen concentration of the controlled atmosphere adjacent to the first electrode 146, the voltmeter 166 detects an electromotive force (potential difference) which is induced between the first and fourth electrodes 146, 148, according to the principle of a concentration cell. In this specific embodiment, a distance L between the first and second electrodes 146, 160 is approximately 300 microns, while a distance l between the first electrode 146 and the tip of the upraised portion (periphery of the round hole 142) of the insulating layer 134 is approximately 60 microns.

Figure 26:
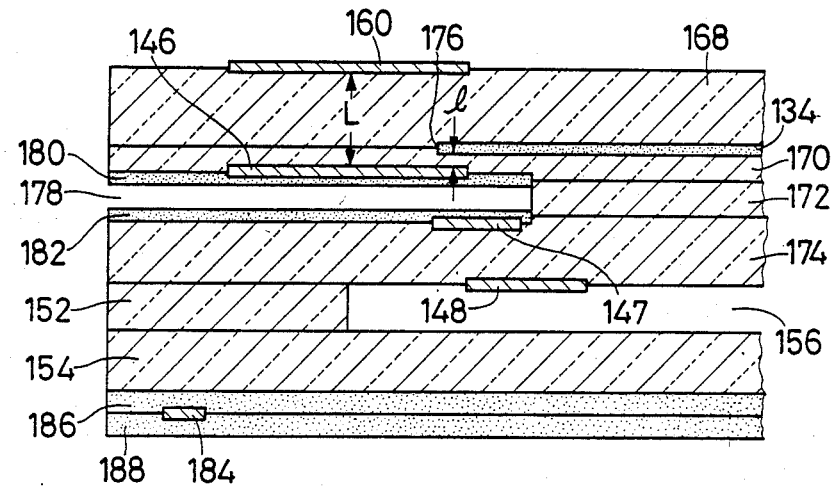
FIG. 26 is a cross sectional view taken along line 26—26 of FIG. 25.
Figure 25:
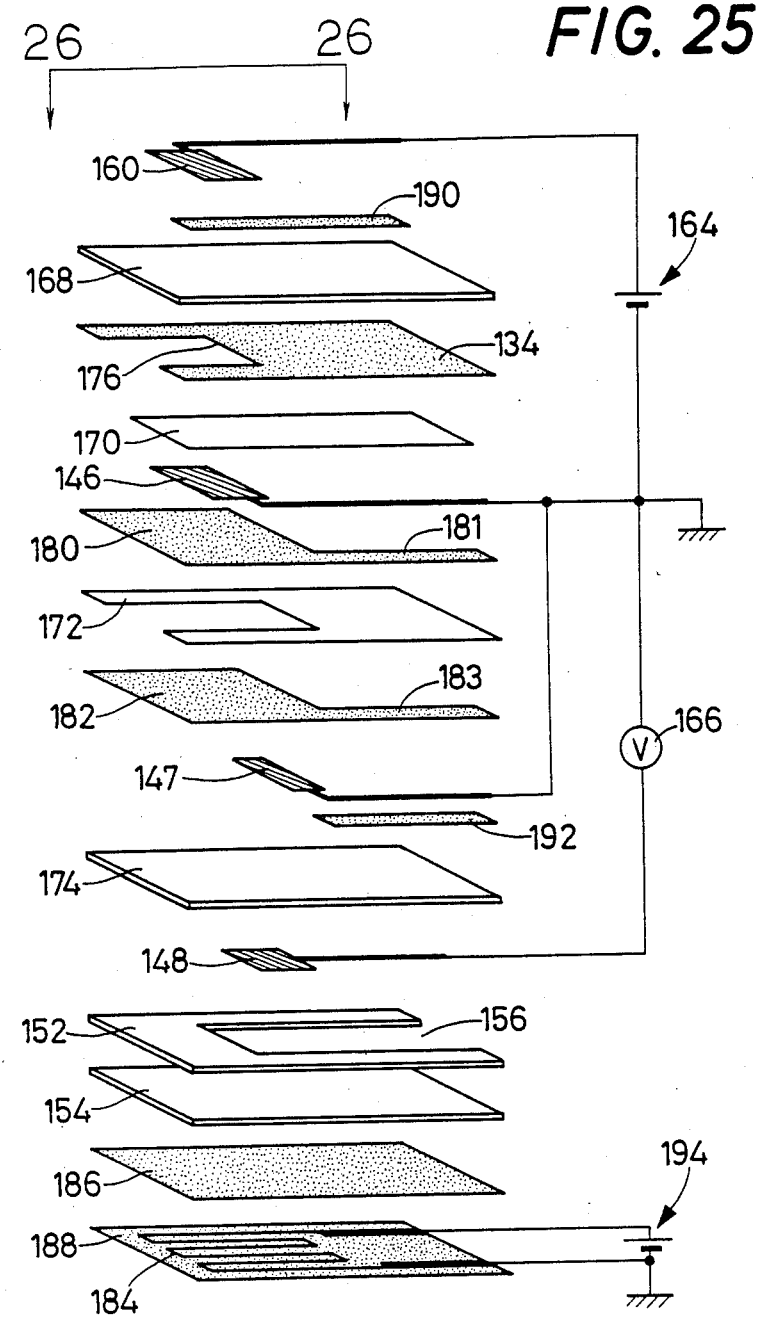
FIG. 25 is an exploded perspective view showing a yet further embodiment of the invention.

There is shown in FIGS. 25 and 26 another form of electrochemical device, which is constructed according to the basic arrangement of FIG. 4. This electrochemical device uses a laminar stack of solid electrolyte which consists of four solid electrolyte layers 168, 170, 172 and 174, and the spacer and covering members 152 and 154. Between the solid electrolyte layers 168, 170, is interposed an insulating layer 134 which has a rectangular cutout 176. The insulating layer 134 electrically separates the laminar stack of solid electrolyte into two portions, one on the side of the second electrode 148, and the other on the side of the fourth electrode 160. The solid electrolyte layer 172 has a rectangular cutout which cooperates with the upper and lower solid electrolyte layers 170, 174 to define a thin flat space 178 which is open to the external space in which the gas to be measured exists. This thin flat space 178 serves as diffusion-resistance means.

On portions of the opposite surfaces of the solid electrolyte layers 170, 174 which correspond to the thin flat space 178, there are formed the first and third electrodes 146, 147, respectively. These first and third electrodes 146, 147 are electrically connected to each other at a point outside the electrochemical element. The third electrode 147 is positioned inwardly of the first electrode 146, i.e., positioned a more distance away from the open end of the thin flat space 178, than the first electrode 146, as indicted in FIG. 26. The first and third electrodes 146, 147 are protected by respective porous protective layers 180, 182 having an electrical insulating property, whereby these electrodes 146, 147 are exposed through the protective layers 180, 182 to the atmosphere in the thin flat space 178.

On the outer surface of the covering member 154 which cooperates with the spacer member 156 to define the air passage 156, there is formed an electrical heater comprising a heating element 184, and two ceramic layers 186, 188 which sandwich the heating element 184. An electrical lead of the fourth electrode 160 is electrically insulated by an insulating strip 190 from the solid electrolyte layer 168. An electrical lead of the first electrode 146 is electrically insulated by the insulating layer 134 and an extension 181 of the protective layer 180. Further, an electrical lead of the third electrode 147 is electrically insulated by an extension 183 of the protective layer 182 and an insulating strip 192. Reference numeral 194 indicates a power source for energizing the heating element 184.

In the electrochemical device constructed as described above, an electrochemical pumping operation occurs primarily between the first and second electrodes 146, 160, and the contribution of the third electrode 147 to the pumping operation is comparatively small. The voltmeter 166 is adapted to detect a potential difference between the fourth electride 148, and the third electrode 147 (first electrode 146) exposed to the innermost portion of the thin flat space 178 at which the diffusion resistance is the highest. The distance L between the first and second electrodes 146, 160 is about 500 microns, while the distance l between the first electrode 146 and the insulating layer 134 is about 10 microns.

The heating element 184 is energized by the power source 194, to heat the electrochemical element so as to maintain suitable operating temperatures of the solid electrolyte layers 168, 170, 172, 174, and the first, second, third and fourth electrodes 146, 160, 147, 148, even when the temperature of the gas to be measured is low.

Figure 27:
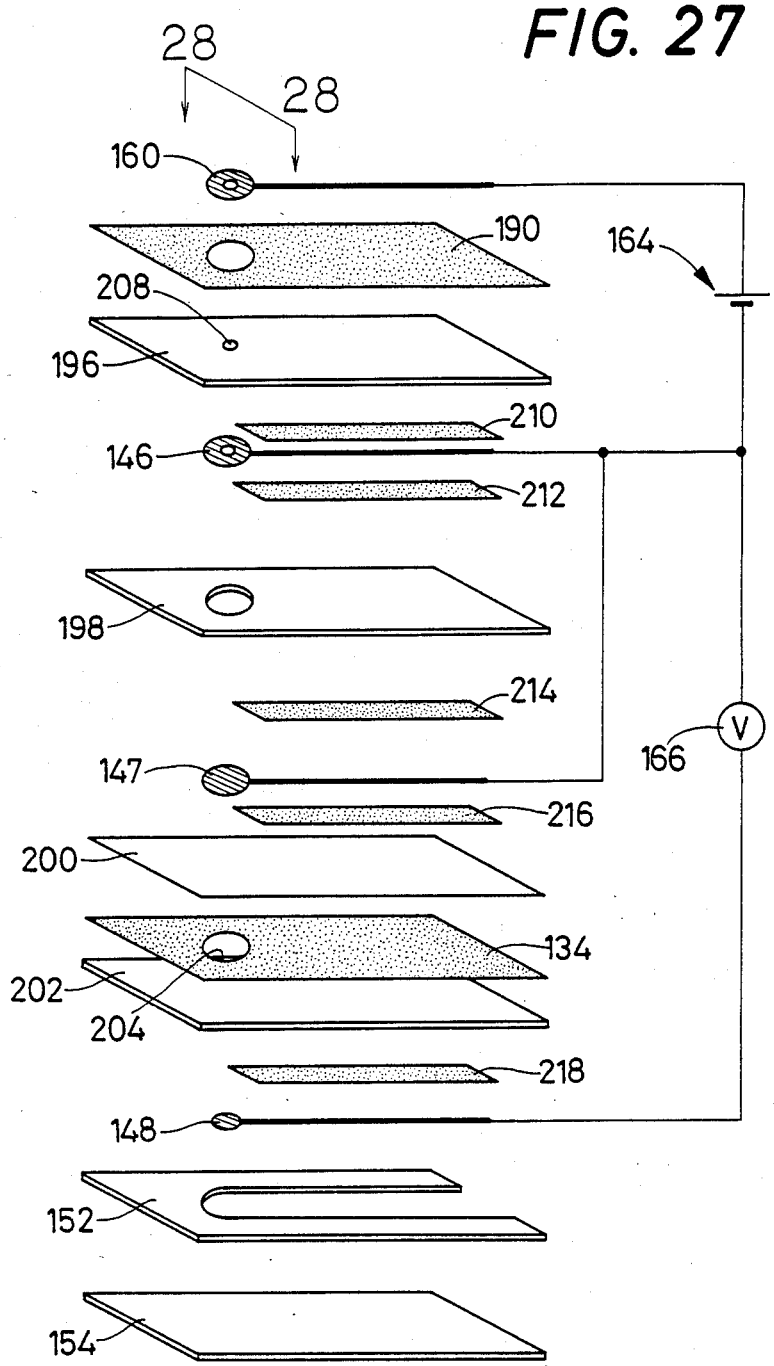
FIG. 27 is an exploded perspective view showing a still further embodiment of the invention.
Figure 28:
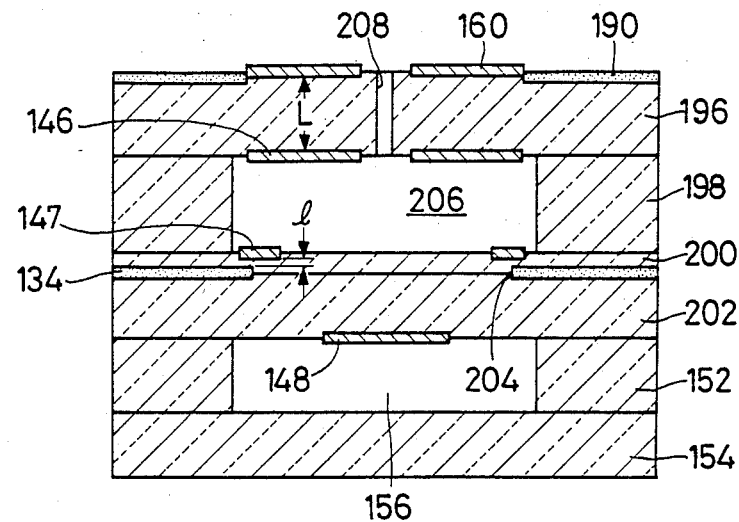
FIG. 28 is a cross sectional veiw taken along line 28—28 of FIG. 27.

A further example of the electrochemical device of the invention is illustrated in FIGS. 27, 28, which is constructed according to the basic arrangement shown in FIG. 8. Like the preceding example, this example employs a laminar stack of solid electrolyte which consists of four solid electrolyte layers 196, 198, 200, 202, and the spacer and covering members 152, 154. The laminar stack is electrically divided into two portions (first and second solid electrolyte bodies), by the insulating layer 134 interposed between the solid electrolyte layers 200, 202. The insulating layer 134 has a round opening 204 which is concentric with the third electrode 147 on the adjacent solid electrolyte layer 200. The third electrode 147 is spaced from the insulating layer 134 in the direction of thickness, by a slight distance l; which is about 20 microns in this specific example. In the meantime, the distance L between the first and second electrodes 146, 160 is selected to be about 300 microns.

In the present arrangement, the solid electrolyte layer 198 has a round opening which cooperates with the upper and lower solid electrolyte layers 196, 200 to define an internal cavity 206 having a relatively large volume. The first and third electrodes 146, 147 are exposed to this internal cavity 206. The solid electrolyte layer 196 has an aperture 208 which communicates with the internal cavity 206 and the external space in which the gas to be measured exists. The aperture 208 functions as diffusion-resistance means. In FIG. 27, reference numerals 210, 212, 214, 216 and 218 designate insulating strips for electrical insulation of the leads of the electrodes 146, 147, 148.

Figure 29:
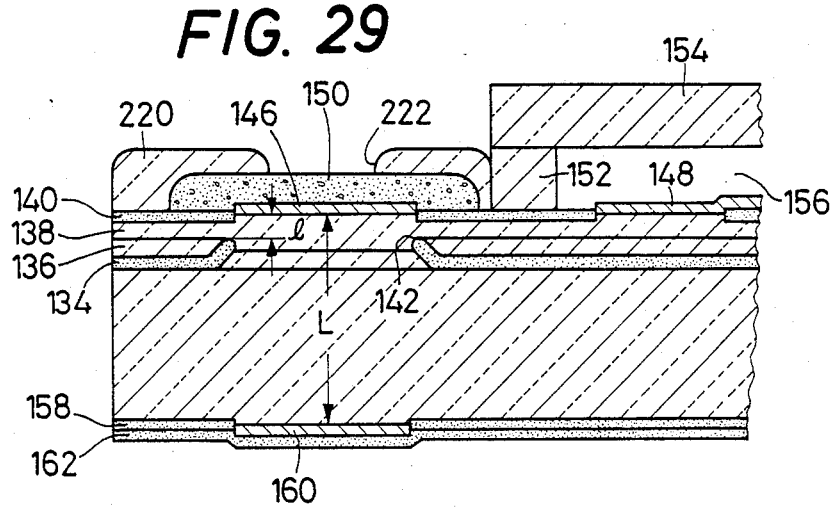
FIG. 29 is a cross sectional view corresponding to FIG. 24, illustrating yet another embodiment of the invention.

FIG. 29 illustrates a yet further example of the electrochemical device, which is a modification of the device of FIGS. 23 and 24. In the instant device, the porous ceramic layer 150 serving as diffusion-resistance means is partly covered with a gas-tight ceramic layer 220 made of a suitable ceramic material. The ceramic layer 220 has an opening 222 which is smaller than the first electrode 146. The first electrode 146 is formed on the surface of the porous ceramic layer 150 remote from the opening 222, so that the electrode 146 and the opening 222 are concentric with each other.

The gas in the external space enters through the opening 222, and diffuses through the porous ceramic layer 150 toward the first electrode 146. The diffusion resistance is the highest adjacent to the peripheral or radially outer portion of the first electrode 146, which is the farthest from the center of the opening 222 in the gas-tight ceramic layer 220, in the direction parallel to the surface of the electrode 147. An electromotive force between the peripheral portion of the electrode 146 (the third electrode) and the fourth electrode 148 is detected.

In the above construction, the distance l between the first electrode 146 and the tip of the upraised portion (periphery of the opening 142) of the insulating layer 134 is selected to be approximately 30 microns. Further, the distance L between the first and second electrodes 146, 160 which perform an electrochemical pumping operation is selected to be approximately 300 microns. This dimensional arrangement is effective to prevent deterioration of a portion of the solid electrolyte layer 138 which contacts the first electrode 146, and allows accurate detection of a potential difference between the first and fourth electrodes 146, 148.

As described hitherto, the method of the present invention requires a comparatively small amount of auxiliary electric current to be applied to the electrochemical sensing cell to effect an auxiliary electrochemical pumping operation for controlling the atmosphere surrounding the third electrode of the sensing cell, so as to reduce a difference of partial pressure of the measurement component in the atmosphere adjacent to the third electrode, from that in the atmosphere adjacent to the first electrode of the pumping cell. Thus, the auxiliary pumping action provides for improvement in the measurement accuracy of the electrochemical device, and protection of the solid electrolyte body against deterioration, even when the concentration of a component to be measured in a gas is relatively high.

The electrochemical device constructed according to the invention is characerized in that the first and second solid electrolyte bodies are electrically separated or insulated by electrically resistant means having an opening which is located adjacent to the first or third electrode exposed to the atmosphere that is controlled by means of an electrochemical pumping operation. This arrangement makes it possible to determine the partial pressure of the component to be measured or the component which reacts with the component to be measured in the atmosphere adjacent to the first or third electrode, by detecting a potential difference between the fourth electrode, and the first or third electrode which is one of the two electrodes between which the electrochemical pumping operation is effected. Hence, the electrochemical device according to the invention is capable of effecting the measurement with minimum reduction in the detecting accuracy, and with minimum deterioration of a portion of the solid electrolyte body adjacent to the first electrode.

Thus, the present invention is effective to improve the durability of the electrochemical element or device, even if the element or device is used to detect such gases that would cause severe deterioration of the solid electrolyte body on the conventional element or device. In particular, the advantage of the present invention is prominent, especially when the invention is practiced on or embodied as an oxygen sensor which is used to detect the oxygen concentration of the atmosphere (i.e., ambient air), with a comparatively large amount of pumping current applied to the pumping cell to control the high concentration of oxygen in the atmosphere. The conventional device suffers severe deterioration of its solid electrolyte body when operated under such pumping conditions. According to the present invention, the oxygen sensor may be operated without such inconveniences even when the gas to be measured has a high concentration of a component including conductive ion and inert components. This is an important industrial significance of the present invention.

The electrochemical detecting method or device according to the present invention is suitably practiced or used for determining an air/fuel ratio of an air/fuel mixture supplied to an engine of a motor vehicle, by detecting either lean-burned or rich-burned exhaust gases produced by the engine. However, by exposing the reference electrode to a reference gas such as the ambient air whose oxygen concentration is constant, the instant method or device permits highly accurate measurement of exhaust gases whose composition is continuously varied over a wide range, from the lean-burned condition to the rich-burned condition, depending upon the varying air/fuel ratio of the air/fuel mixture. Further, the present invention may be embodied as sensors or controllers, or methods for determining or controlling the concentration of nitrogen, carbon dioxide, hydrogen and other components in the air, other than oxygen, which are associated with electrode reaction. Furthermore, the invention is applicable to humidity sensors using a proton-conductive material.

What is claimed is:

1. A method of determining the concentration of a component in a gas, by an electrochemical element which includes: an electrochemical pumping cell comprising a first solid electrolyte body, and a first and a second porous electrode disposed on the first electrolyte body; an electrochemical sensing cell comprising a second solid electrolye body, and a third and a fourth porous electrode disposed on the second solid electrolyte body, said third electrode being positioned near said first electrode of the pumping cell; and diffusion-resistance means having a predetermined diffusion resistance to the molecules of said component in the gas in an external space, said diffusion-resistance means permitting the gas to diffuse therethrough with said diffusion resistance, for contact with said first and third electrodes of the pumping and sensing cells, the method comprising a step of controlling a pumping current to be applied to said pumping cell to effect an electrochemical pumping operation, so that an electromotive force which is induced on said sensing cell, according to the principle of a concentration cell, based on a partial pressure of said component in an atmosphere adjacent to said third electrode, coincides with a predetermined value, a step of detecting the controlled pumping current, and a step of determining the concentration of said component in the gas, based on the detected pumping current, said method further comprising the step of:

applying an auxiliary pumping current between said third electrode of the sensing cell, and one of the other electrodes, for effecting an auxiliary pumping operation so as to change the partial pressure of said component in the atmosphere adjacent to said third electrode, in a direction in which the partial pressure of said component in an atmosphere adjacent to said first electrode is changed by said electrochemical pumping operation of said pumping cell.

2. A method according to claim 1, wherein said first electrode of the pumping cell and said third electrode of the sensing cell are substantially exposed to an internal cavity formed in said electrochemical element, said internal cavity communicating with said external space through said diffusion-resistance means.

3. A method according to claim 2, wherein said internal cavity to which said first and third electrodes are exposed functions substantially as said diffusion-resistance means, and communicates with said external space.

4. A method according to claim 2, wherein said internal cavity to which said first and third electrodes are exposed is filled with a porous filler whose diffusion resistance is lower than said predetermined diffusion resistance of said diffusion-resistance means.

5. A method according to claim 1, wherein at least one of said first and second solid electrolyte bodies of said pumping and sensing cells is a porous layer which has said predetermined diffusion resistance and functions as said diffusion-resistance means.

6. A method according to claim 1, wherein said fourth electrode of the sensing cell is exposed to a reference gas.

7. A method according to claim 1, wherein the amount of said auxiliary pumping current applied between said third electrode and said one of the other electrodes is proportional to the amount of said pumping current applied to said pumping cell.

8. A method according to claim 1, wherein said auxiliary pumping current applied between said third electrode and said one of the other electrodes is changed as a function of said pumping current applied to said pumping cell, an amount of said auxiliary pumping current being controlled so that a magnitude of resistance polarization caused by said auxiliary pumping is not greater than 50% of said electromotive force induced on said sensing cell according to the principle of a concentration cell, and so that the amount of said auxiliary pumping current is effective to achieve said auxiliary pumping operation.

9. A method according to claim 1, wherein said first and second solid electrolyte bodies of said pumping and sensing cells are electrically connected to each other, while said third electrode of the sensing cell is electrically connected to said first electrode of the pumping cell, a part of said pumping current applied to said pumping cell being permitted to flow through said third electrode of the sensing cell through a connection of said first and second solid electrolyte bodies, and a connection of said first and third electrodes.

10. A method according to claim 9, wherein different portions of a single common electrode serve as said first and third electrodes.

11. A method according to claim 9, wherein said first and third electrodes are electrically connected to each other through a resistor having a predetermined resistance.

12. A method according to claim 11, wherein a single common electrode serves as said second and fourth electrodes.

13. A method according to claim 1, wherein said first and second solid electrolyte bodies of said pumping and sensing cells are electrically connected to each other, while a DC power source is connected between said third electrode of the sensing cell and said first electrode of the pumping cell, for applying a DC current as said auxiliary pumping current between said first and third electrodes, said first electrode functioning as said one of the other electrodes.

14. A method according to claim 1, wherein a DC power source is connected to said third and fourth electrodes, for applying a DC current as said auxiliary pumping current between said third and fourth electrodes of the sensing cell, said fourth electrode functioning as said one of the other electrodes.

15. A method according to claim 14, wherein different portions of a single common electrode serves as said first and third electrodes.

16. A method according to claim 1, wherein the concentration of said component in the gas is determined by detecting a sum of a current flowing through said first electrode of the pumping cell, and a current flowing through said third electrode of the sensing cell.

17. An electrochemical device for determining the concentration of a component in a gas in an external space, including: an electrochemical pumping cell comprising a first solid electrolyte body, and a first and a second porous electrode disposed on the first solid electrolyte body; an electrochemical sensing cell comprising a second solid electrolyte body, and a third and a fourth porous electrode disposed on the second solid electrolyte body, said third electrode being positioned near said first electrode of the pumping cell and being electrically connected to said first electrode of the pumping cell, and diffusion-resistance means having a predetermined diffusion resistance to the molecules of said component in the gas in an external space, said diffusion-resistance means permitting the gas to diffuse therethrough with said diffusion resistance, for contact with said first and third electrodes of the pumping and sensing cells; means for applying a pumping current between said first and second electrodes of the pumping cell to effect an electrochemical pumping operation, for controlling a partial pressure of said component in an atmosphere adjacent to said first electrode; and means for detecting a potential difference which is induced between said third and fourth electrodes, due to a difference between the controlled partial pressure of the component in said atmosphere adjacent to said third electrode, and a partial pressure of the component in said atmosphere adjacent to said fourth electrode, said pumping and sensing cells forming an electrochemical element, said electrochemical device comprising:

electrically resistant means which electrically separates said first and second solid electrolyte bodies from each other, said electrically resistant means having an opening which is located adjacent to at least one of said first and third electrodes and which permits said first and second solid electrolyte bodies to be electrically connected partially to each other, whereby said potential difference between said third and fourth electrodes is detected.

18. An electrochemical device according to claim 17, wherein different portions of a single common electrode serve as said first and third electrodes.

19. An electrochemical device according to claim 17, wherein said opening of said electrically resistant means is located adjacent to a portion of said first electrode at which a resistance to diffusion of said component through said diffusion-resistance means is the highest.

20. An electrochemical device according to claim 17, wherein said electrically resistant means consists of an electrically insulating layer which is formed within a laminar structure of said electrochemical element.

21. An electrochemical device according to claim 17, wherein said electrochemical element has an internal cavity to which said first and third electrodes are substantially exposed, and which communicates with said external space through said diffusion-resistance means.

22. An electrochemical device according to claim 17, wherein said electrochemical element has an internal cavity to which said first electrode is substantially exposed, said internal cavity directly or indirectly communicating with said external space and having a predetermined diffusion resistance to the molecules of said component in the gas.

23. An electrochemical device according to claim 17, wherein said diffusion-resistance means consists of a porous layer formed so as to cover said first and third electrodes on said first and second solid electrolyte bodies.

24. An electrochemical device according to claim 23, wherein said porous layer is made of a solid electrolyte material substantially similar chemical composition to said first or second solid electrolyte body.

25. An electrochemical device according to claim 23, wherein said electrochemical element comprises a gas-tight layer which is formed on said porous layer, and which has an opening which is smaller than said first electrode, said gas-tight layer being positioned such that said opening is aligned with said first electrode, so as to permit said gas in said external space to be introduced through said opening, for diffusion through said porous layer toward said first electrode.

26. An electrochemical device according to claim 17, wherein said electrochemical element has an internal space in which said reference gas exists, said fourth electrode being positioned on said second solid electrolyte body such that the fourth electrode is exposed to said reference gas.

27. An electrochemical device according to claim 17, further comprising an electrical heater in the form of a layer disposed on a laminar structure of said electrochemical element, to maintain said first and second solid electrolyte bodies at elevated operating temperatures.

* * * * *